(12) United States Patent
Haley et al.

(10) Patent No.: US 8,575,218 B2
(45) Date of Patent: Nov. 5, 2013

(54) THIOL-CONTAINING COMPOUNDS FOR THE REMOVAL OF ELEMENTS FROM TISSUES AND FORMULATIONS THEREFOR

(75) Inventors: Boyd E. Haley, Nicholasville, KY (US); David A. Atwood, Lexington, KY (US); Niladri Gupta, Georgetown, KY (US)

(73) Assignee: The University of Kentucky Research Foundation, Lexington, KY (US)

( * ) Notice: Subject to any disclaimer, the term of this patent is extended or adjusted under 35 U.S.C. 154(b) by 196 days.

(21) Appl. No.: 13/041,798

(22) Filed: Mar. 7, 2011

(65) Prior Publication Data

US 2011/0160150 A1    Jun. 30, 2011

Related U.S. Application Data

(63) Continuation-in-part of application No. 12/892,464, filed on Sep. 28, 2010, which is a continuation of application No. PCT/US2010/050512, filed on Sep. 28, 2010.

(60) Provisional application No. 61/246,278, filed on Sep. 28, 2009, provisional application No. 61/246,282, filed on Sep. 28, 2009, provisional application No. 61/246,360, filed on Sep. 28, 2009.

(51) Int. Cl.
   *A01N 37/12*   (2006.01)
   *A01N 37/10*   (2006.01)
   *A01N 43/00*   (2006.01)

(52) U.S. Cl.
   USPC ................. 514/562; 514/568; 514/183

(58) Field of Classification Search
   None
   See application file for complete search history.

(56) References Cited

U.S. PATENT DOCUMENTS

| | | |
|---|---|---|
| 4,039,446 A | 8/1977 | Ban et al. |
| 4,281,086 A | 7/1981 | Gaul, Jr. et al. |
| 4,433,154 A | 2/1984 | Hirai |
| 4,508,838 A | 4/1985 | Buckl |
| 4,673,562 A | 6/1987 | Davison et al. |
| 4,751,286 A | 6/1988 | Packard et al. |
| 4,969,995 A | 11/1990 | Jackson et al. |
| 5,073,575 A | 12/1991 | Blanch et al. |
| 5,173,470 A | 12/1992 | Bruening et al. |
| 5,200,473 A | 4/1993 | Jeanneret-Gris |
| 5,494,935 A | 2/1996 | Miller et al. |
| 5,615,862 A | 4/1997 | Gaudette |
| 5,766,478 A | 6/1998 | Smith et al. |
| 6,013,246 A | 1/2000 | Langworth |
| 6,025,140 A | 2/2000 | Langel et al. |
| 6,586,600 B2 | 7/2003 | Atwood et al. |
| 6,852,369 B1 | 2/2005 | Atwood et al. |
| 6,936,729 B2 | 8/2005 | Wolff et al. |
| 7,087,770 B2 | 8/2006 | Wolff et al. |
| 7,417,034 B2 | 8/2008 | Susilo |
| 7,482,160 B2 | 1/2009 | Monahan et al. |
| 2002/0136763 A1 | 9/2002 | Demopoulos et al. |
| 2004/0132101 A1 | 7/2004 | Lazar et al. |
| 2006/0099239 A1 | 5/2006 | Coleman et al. |
| 2006/0269488 A1 | 11/2006 | Ott |
| 2007/0026109 A1 | 2/2007 | Foulger |
| 2007/0077586 A1 | 4/2007 | Baggot |
| 2007/0191281 A1 | 8/2007 | Wolff et al. |
| 2010/0227812 A1 | 9/2010 | Haley et al. |
| 2011/0076246 A1 | 3/2011 | Haley et al. |
| 2011/0237525 A1 | 9/2011 | Haley et al. |

FOREIGN PATENT DOCUMENTS

EP    0 057 797    8/1982

OTHER PUBLICATIONS

Anderson et al, "Molecular Mechanisms of in Vivo Metal Chelation: Implications for Clinical Treatment of Metal Intoxications," Environ. Health Perspect., vol. 110, Suppl. 5, pp. 887-890 (2002).*

(Continued)

*Primary Examiner* — Frederick Krass
*Assistant Examiner* — Dennis J Parad
(74) *Attorney, Agent, or Firm* — King & Schickli, PLLC

(57) ABSTRACT

Methods and pharmaceutical formulations for ameliorating heavy metal toxicity and/or oxidative stress are disclosed, comprising administering pharmaceutically effective amounts of ligands according to the present disclosure. The ligands are of the general structure:

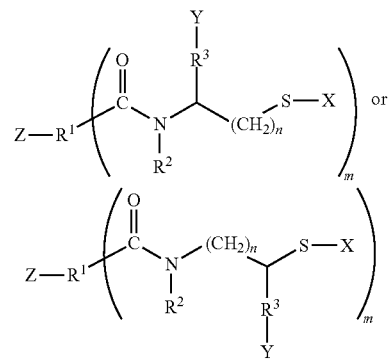

where $R^1$ comprises benzene, pyridine, pyridin-4-one, naphthalene, anthracene, phenanthrene or alkyl groups, $R^2$ comprises hydrogen, alkyls, aryls, a carboxyl group, carboxylate esters, organic groups or biological groups, $R^3$ comprises alkyls, aryls, a carboxyl group, carboxylate esters, organic groups or biological groups, X comprises hydrogen, lithium, sodium, potassium, rubidium, cesium, francium, alkyls, aryls, a carboxyl group, carboxylate esters, thiophosphate, N-acetyl cysteine, mercaptoacetic acid, mercaptopropionic acid, thiolsalicylate, organic groups or biological groups, n independently equals 1-10, m=1-6, Y comprises hydrogen, polymers, silicas or silica supported substrates, and Z comprises hydrogen, alkyls, aryls, a carboxyl group, carboxylate esters, a hydroxyl group, $NH_2$, $HSO_3$, halogens, a carbonyl group, organic groups, biological groups, polymers, silicas or silica supported substrates.

25 Claims, 7 Drawing Sheets

(56) References Cited

OTHER PUBLICATIONS

Hutchison, "The Design and Synthesis of Novel Chelates for the Precipitation of Mercury," University of Kentucky Doctoral Dissertations, Paper 519, pp. 1-154 (170 total pages) (2007).*

Uwe Schröder, Lothar Beyer, and Joachim Sieler "Synthesis and X-ray structure of a new silver(I) coordination polymer assembled as one-dimensional chains" Inorganic Chemistry Communications vol. 3, Issue 11, Nov. 2000, pp. 630-633.

Matthew M. Matlock, Brock S. Howerton and David A. Atwood "Irreversible precipitation of mercury and lead" Journal of Hazardous Materials vol. 84, Issue 1, Jun. 1, 2001, pp. 73-82.

Matthew M. Matlock, Brock S. Howerton, Kevin R. Henke and David A. Atwood "A pyridine-thiol ligand with multiple bonding sites for heavy metal precipitation" Journal of Hazardous Materials vol. 82, Issue 1, Mar. 19, 2001, pp. 55-63.

Paul Römkens, Lucas Bouwman, Jan Japenga and Cathrina Draaisma "Potentials and drawbacks of chelate-enhanced phytoremediation of soils" Environmental Pollution vol. 116, Issue 1, Jan. 2002, pp. 109-121.

PCT/US2010/050512 International Search Report dated Jun. 21, 2011.

PCT/US2010/050512 Written Opinion dated Jun. 21, 2011.

Gelinsky, M. et al., Tripodal Pseudopeptides with Three Histidine or Cysteine Donors: Synthesis and Zinc Complexation, Inorg. Chem. 2002, 41, 2560-2564 (Apr. 5, 2002).

Ludlow, F.R. et al., Two-Vial, LC-MS Identifiction of Ephedrine Receptors froma Solution-Phase Dynamic Combinatorial Library of over 9000 Components J. Am. Chem. Soc. 2008, 130, 12218-12219 (Aug. 21, 2008).

West, K.R. et al., Dynamic Cominatorial Libraries of Disulfide Cages in Water, Organic Letters, 2005, 7(13), 2615-2618 (May 26, 2005) See Compound 5.

Wallen, E.A.A. et al., New Prolyl Oligopeptidase Inhibitors Developed from Dicarboxylic Acid Bis (L-prolyl-pyrrolidine) Amides, J. Med. Chem. 2003, 46, 4543-4551 (Sep. 4, 2003).

William D. Roll; "Synthesis of Potential Antineoplastic Agents I"; Journal of Pharmaceutical Science, Jun. 1964, vol. 53, No. 6, pp. 686-688.

International Preliminary Report on Patentability for International Application No. PCT/US2010/050512 dated Apr. 3, 2012.

Tandon et al.; "Chelation in Metal Intoxication XXXVIII: Effect of Structurally Different Chelating Agents in Treatment of Nickel Intoxication in Rat"; Fundamental and Applied Toxicology, vol. 31, 141-148 (1996).

Anderson, Ole; "Principles and Recent Developments in Chelation Treatment of Metal Intoxication"; Chemical Reviews (1999) vol. 99, 2683-2710.

Non-Final Office Action for U.S. Appl. No. 12/731,415 dated May 24, 2012.

Non-Final Office Action for U.S. Appl. No. 12/630,259 dated Nov. 21, 2011.

Final Office Action for U.S. Appl. No. 12/630,259 dated Apr. 25, 2012.

Yamada et al.; "Solid-Phase Synthesis of Dehydroalanine Derivatives"; Tetrahedron Letters (1998), vol. 39, Issue 3-4, pp. 289-292.

Kudo et al.; "Efficient Synthesis of Macrocycles by Oxidation of Cysteine-Based Dithiols"; Tetrahedron Letters (2001), vol. 42, Issue 44, pp. 7847-7850.

Non-Final Office Action for U.S. Appl. No. 12/892,464 dated Feb. 2, 2012.

Non-Final Office Action for U.S. Appl. No. 13/565,047 dated Nov. 8, 2012.

Final Office Action for U.S. Appl. No. 12/892,464 dated Nov. 28, 2012.

* cited by examiner

THIOL-CONTAINING COMPOUNDS FOR THE REMOVAL OF ELEMENTS FROM TISSUES AND FORMULATIONS THEREFOR

CROSS REFERENCE TO RELATED APPLICATIONS

This application is a continuation-in-part of U.S. patent application Ser. No. 12/892,464, filed on Sep. 28, 2010, which in turn is a continuation of international patent application no. PCT/US10/50512, filed on Sep. 28, 2010 and claiming the benefit of priority in U.S. Provisional Application Ser. Nos. 61/246,278, 61/246,282 and 61/246,360, all three filed on Sep. 28, 2009, the entire disclosures of each of which are incorporated herein in their entirety.

FIELD OF THE INVENTION

The present invention relates to compounds utilized in covalent binding to a wide range of metals and main group elements, and more specifically to sulfur-containing ligands and the utilization of such to remove contaminants from solids, liquids and gases.

BACKGROUND OF THE INVENTION

Heavy metal and main group element pollution is an existing and growing worldwide problem. During the past few decades, federal and state governments have instituted environmental regulations to protect the quality of surface and ground water from contaminants. In response to these regulatory requirements, numerous products have been developed to precipitate contaminants from surface water, ground water and soil. Examples of compositions and methods utilized in precipitating metals from water and soil are detailed in U.S. Pat. No. 6,586,600, the entire disclosure of which is hereby incorporated by reference.

There are numerous industrial and environmental situations where ligands capable of binding metals and main group elements can be utilized for remediation purposes. For example, waste water issuing from waste treatment facilities, chlor-alkali industries, metal finishing industries and certain municipal landfills often present contamination problems. Similarly, the metal content of water exiting both functional and abandoned mines is a significant environmental issue in geographical areas with a heavy mining industry. Soil and surface waters located in areas near natural gas pump houses suffer a similar metal contamination problem. Gasses emitted from coal-fired power plants and the incineration of municipal and medical waste contain mercury. Thus, there is a need for ligands capable of binding and removing metals and main group elements from gasses, aqueous and non-aqueous solutions and solid substrates.

It is known in the art to use sulfur-containing compounds to bind heavy metals. For example, Thio-Red® is a chemical reagent used for precipitating divalent heavy metals from water. This product is a complex aqueous solution of sodium (with or without potassium) thiocarbonate, sulfides, and other sulfur species. Thio-Red® ultimately removes Cu, Hg, Pb, and Zn from aqueous solutions through the formation of metal sulfides (i.e. CuS, HgS, PbS, and ZnS), rather than metal thiocarbonates. Sodium and potassium dialkyldithiocarbamates such as HMP-2000®, are also widely used as metal precipitants. However, the limited ability of most reagents presently used on a commercial basis to form stable, covalent bonds with heavy metals is a major concern for remediation applications. Reagents that lack sufficient or metal-specific binding sites may produce metal precipitates that are unstable over time and under certain pH conditions. Such unstable precipitates may release bound metal back into the environment, thereby proving unsatisfactory as treatment or remediation agents. Further, these reagents may form simple metal sulfides which bacteria are capable of methylating (in the case of Hg, forming the water-soluble cation, MeHg$^+$). Accordingly, there is a need for ligands which not only bind metals and main group elements, but also bind these elements in such a manner as to form stable, insoluble precipitates which retain the contaminant element(s) over a wide range of environmental conditions and over extended periods of time.

Likewise, it is known to use a variety of chelators for chelation therapy of metals. Many studies today reflect the increasing exposure of the population to mercury and other toxic heavy metals. Examples of currently approved binders for treating heavy metal toxicity such as mercury toxicity are dimercaptopropanesulfonate (DMPS) and dimercaptosuccinic acid (DMSA), which were introduced during World War II to combat industrial exposure to heavy metals. Conventional compounds such as DMPS and DMSA, while often referred to as "chelators," are not truly chelators in the chemical sense of the word. This is because there is insufficient space between the sulfurs on adjacent carbon atoms to allow a large metal atom to bind to both sulfurs at the same time, which is a requirement for forming a true "chelate." Rather, DMPS and DMSA form bound sandwich complexes with metal, where for example two binder molecules bind to a single mercury atom. This provides a weaker attachment than would be the case with a true chelator, which would form two bonds between the thiol (—SH) groups and the HG$^{2+}$. Also, based on their negatively charged properties, binders like DMSA, DMPS and EDTA have a non-specific attraction for all metal ions, including the essential metals Ca$^{2+}$, Mg$^{2+}$, Mn$^{2+}$, etc. The rapid excretion of these binders from the body through the urine can have the negative effect of depleting the body of these essential metals. Deaths have occurred by essential metal depletion by charged binding compounds during a process called chelation therapy, and this medical treatment must therefore be done by an experienced physician.

Heavy metals such as mercury are typically lipid-soluble or can pass through the cell membrane via native divalent metal ion carriers (e.g. for Ca$^{2+}$, Mg$^{2+}$) as the M$^{2+}$ form, and may therefore concentrate intracellularly and more so in the adipose, or fatty, tissue or in other tissues high in lipid content, including without limitation the central nervous system. Indeed, mercury and other heavy metals preferentially partition to and concentrate in the hydrophobic aspects of mammals, fish, and the like, such as fatty tissues, cell membranes, lipid-containing areas of the interior of a cell, and the like.

Thus, the currently available, approved heavy metal binders have several disadvantages with regard to their overall chemical nature that could be improved on by the synthesis of better-designed, true chelators that have safer excretory properties such as higher affinity for the metals and/or main group elements and excretion through the feces instead of the urine. Such better-designed, true chelators would desirably be uncharged, lipid-soluble or hydrophobic compounds, or alternatively convertible from water soluble (for suitability for delivery via the bloodstream) to lipid-soluble compounds in the body, to allow them to partition into the fatty (hydrophobic) tissues where the mercury or other heavy metal burden is primarily located. Further, such chelators would possess low or, better yet, no observable toxicity to mammals alone in the absence of heavy metal exposures. They would be true chelators that would bind heavy metals and main group elements exceptionally tightly, preventing toxic effects and also preventing release or concentration in toxic form in any organ of the body. Still further, desirably the chelators would be excreted through the biliary transport system of the liver into the feces instead of through the kidneys (a very sensitive organ to heavy metal exposure) and into the urine. Still yet further, it would be desirable to provide improved chelators which readily convert between water-soluble and lipid-soluble forms, allowing excretion by the desired route, i.e., via the kidney for the water-soluble form and via the biliary transport system of the liver into the feces for the lipid-soluble form.

SUMMARY OF THE INVENTION

In one embodiment, chelate ligands are of the general formula:

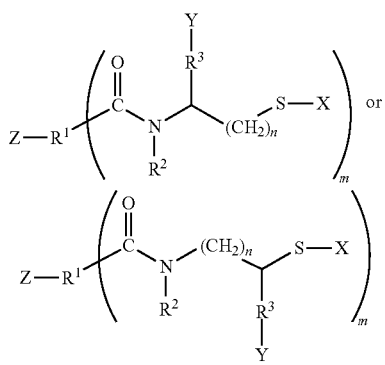

where $R^1$ is selected from a group including benzene, pyridine, pyridin-4-one, naphthalene, anthracene, phenanthrene and alkyl groups, $R^2$ is independently selected from a group including hydrogen, alkyls, aryls, a carboxyl group, carboxylate esters, organic groups and biological groups, $R^3$ is independently selected from a group including alkyls, aryls, a carboxyl group, carboxylate esters, organic groups and biological groups, X is independently selected from a group including hydrogen, lithium, sodium, potassium, rubidium, cesium, francium, alkyls, aryls, a carboxyl group, carboxylate esters, cysteine, homocysteine, glutathione, lipoic acid, dihydrolipoic acid, thiophosphate, N-acetyl cysteine, mercaptoacetic acid, mercaptopropionic acid, γ-glutamyl cysteine, phytochelatins, thiolsalicylate, organic groups and biological groups, n independently equals 1-10, m=1-6, Y is independently selected from a group including hydrogen, polymers, silicas and silica supported substrates, and Z is selected from a group including hydrogen, alkyls, aryls, a carboxyl group, carboxylate esters, a hydroxyl group, $NH_2$, $HSO_3$, halogens, a carbonyl group, organic groups, biological groups, polymers, silicas and silica supported substrates, with the proviso that when $R^1$ represents an alkyl group, at least one X cannot simultaneously represent hydrogen.

In another aspect, the present invention relates to methods of removing metals and/or main group elements from a starting material. The methods comprise contacting a starting material with an effective amount of a sulfur-containing chelate ligand as described above for a sufficient time to form a stable ligand-metal and/or ligand-main group element complex(es), said metal and/or main group element complex(es) remaining essentially irreversibly bound to said ligand over a range of acidic and basic pH values.

In another aspect, the present invention relates to methods of removing metals and/or main group elements from a lipid-containing tissue in a human and/or animal body. The methods comprise intravenously delivering an amount of a sulfur-containing chelate ligand as described above to a lipid-containing tissue in a body, forming a ligand-metal and/or ligand-main group element complex(es), and excreting the complex(es) from the body. We have observed that certain prior art uncharged, hydrophobic compounds, such as those disclosed in U.S. Pat. No. 6,586,600 to Atwood et al., have exceptionally low toxicity when injected or ingested by test animals. Disadvantageously, the water-insolubility of these hydrophobic compounds makes them poor candidates for intravenous applications. Intravenous (IV) application has the advantage of speed of general delivery and the ability to treat an unconscious patient. Therefore, in the present disclosure, analogs of uncharged, non-toxic chelators are described which may initially be provided as charged, water soluble compounds. These water-soluble compounds are converted in the blood to uncharged lipid soluble compounds which can enter the membranes and other hydrophobic aspects of cells and tissues, and even cross the blood brain barrier.

Further, the present disclosure provides uncharged, non-toxic lipid soluble analogs that can be converted by intracellular enzymes once internalized into water soluble chelators. These same compounds can be treated externally with enzymes (esterases) to make them water soluble for IV applications. This may be especially useful if treatment is required that does not enter cells or cross the blood brain barrier and still retain high heavy metal and/or main group element affinity.

In one embodiment of this aspect, the described chelators are thiol/thiolate compounds including an aromatic ring structure, further including additional functional groups on the organic ring structure and/or on the pendent thiol chains. A representative structure for the compounds is set forth below. In that structure, Z and Y may be a variety of combinations of organic, organometallic and inorganic groups, including without limitation OH, COOH, $NH_2$, $HSO_3$, halogens, and the like. X may be one or more of hydrogen, halogens, organic groups providing thioethers and related derivatives, or metals selected without limitation from the Group 1 and 2 elements recited in the Periodic Table of the Elements, or may include charged molecules having a terminal sulfhydryl include without limitation glutathione, cysteine, homocysteine, lipoic acid, dihydrolipoic acid, thiophosphate, N-acetyl cysteine, mercaptoacetic acid, mercaptopropionic acid, γ-glutamyl cysteine, phytochelatins, thiolsalicylate, and the like. The reference character n may represent any integer from 1-10. Other aromatic groups contemplated include naphthalene, anthracene, phenanthrene, and the like as set forth above.

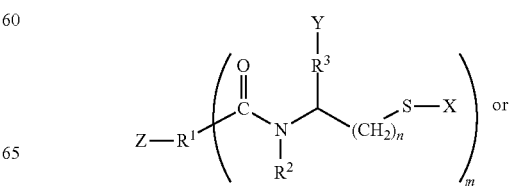

-continued

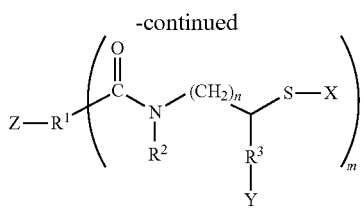

Still further, particular aspects of the present disclosure are directed to pharmaceutically effective amounts and formulations of such chelators for removing metals and/or main group elements from human and/or animal body tissues, such as for ameliorating oxidative stress, treating heavy metal or other toxicity, raising in vivo glutathione levels, as dietary supplements, and the like. The pharmaceutically effective amount of the compounds in question may be administered in any appropriate manner including without limitation oral administration, transdermal administration, nasal administration, intravenous administration, suppository, and others.

As a dietary supplement, methods for such supplementation include orally administering between about 0.5 and about 40.0 mg of compound per kilogram of the mammal's today body weight per day, although due to the lack of toxicity higher dose levels are acceptable. Optionally, the compounds may be administered with one or more additional antioxidants or chelators. Exemplary supplemental antioxidants include without intending any limitation vitamin E, vitamin D, cysteine, cystine, glutathione, lipoic acid, and combinations.

In methods of removing heavy metals or other toxins from mammalian tissues, the compound may be administered in amounts of between about 0.5 mg and about 60.0 mg per kilogram of total body weight per day, although due to the lack of toxicity of the compounds higher doses may be appropriate.

Likewise, in methods for ameliorating oxidative stress, suitable administration routes include administering orally, transdermally, nasally, intravenously, by suppository, or other appropriate routes. The compounds may be administered in amounts of between about 0.5 mg and about 100.0 mg per kilogram of total body weight per day, although due to the lack of toxicity of the compounds higher doses may be appropriate, such as in cases of acute toxicity or high oxidative stress. The compounds may be used to treat oxidative stress resulting from virtually any source or cause, including without limitation heavy metals, drugs such as acetaminophen, xenobiotics, aging, infection, physical injury, and disease.

Other aspects of the present invention will become apparent to those skilled in this art from the following description wherein there is shown and described exemplary embodiments of this invention. As it will be realized, the invention is capable of further embodiments and its several details are capable of modification in various, obvious aspects without departing from the invention. Accordingly, the drawings and descriptions will be regarded as illustrative in nature and not as restrictive.

BRIEF DESCRIPTION OF THE FIGURES

The following detailed description of specific embodiments of the present disclosure can be best understood when read in conjunction with the following drawings, in which.

DETAILED DESCRIPTION OF ILLUSTRATIVE EMBODIMENTS

Figure 1:
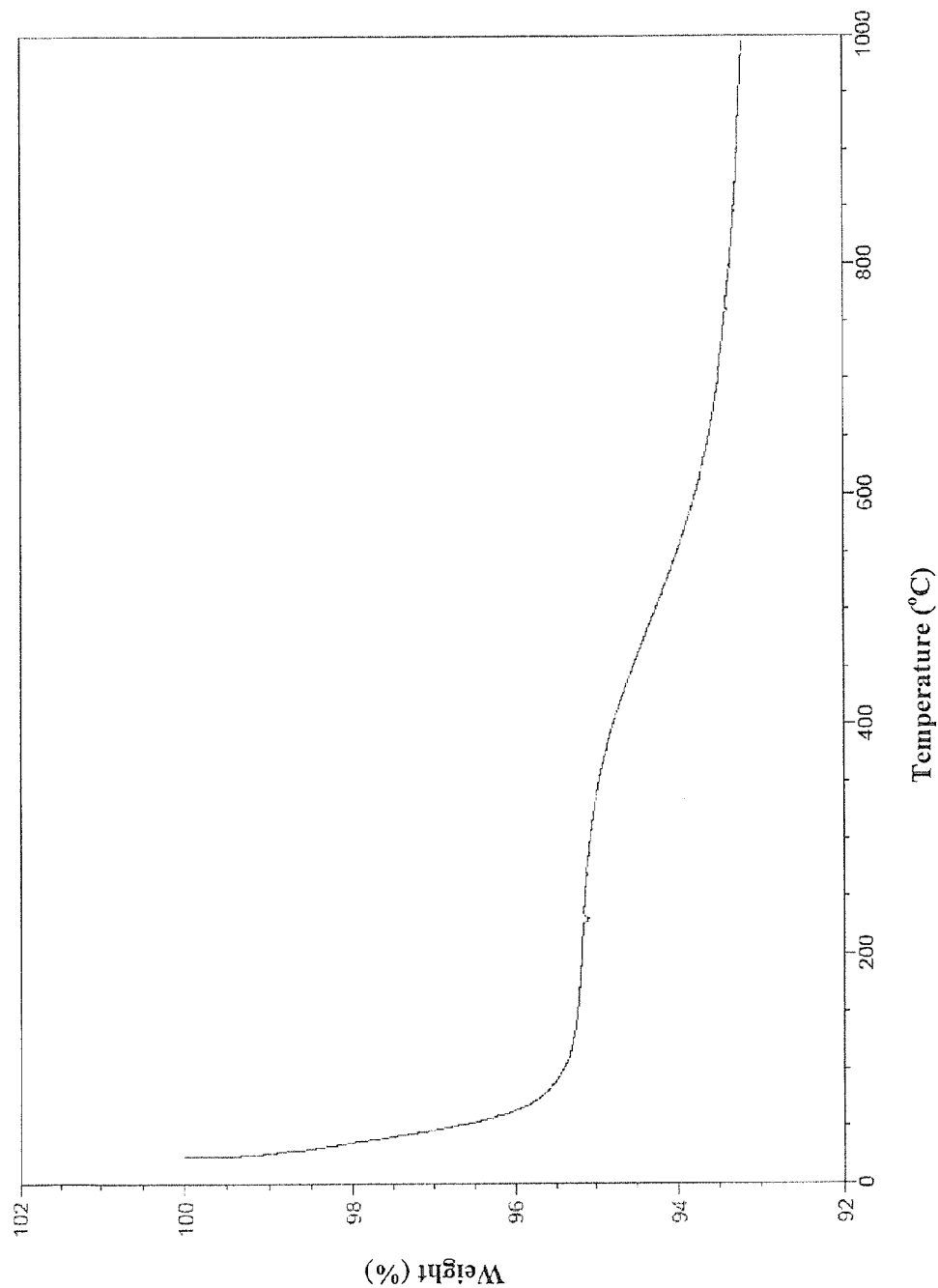
FIG. 1 shows the weight loss results of a thermogravimeteric analysis on Si60 from a temperature range of 30° C. to 1000° C. with a temperature increase of 20° C./min and a flow rate of 110/55 mmHg (inlet/outlet pressure) performed in air atmosphere.

As summarized above, the present invention relates to novel sulfur-containing chelate ligands which bind metals and/or main group elements resulting in ligand-metal and/or ligand-main group element complex(es) which remain stable at a wide range of pH values. In forming the ligand-metal and/or ligand-main group element complex(es), the novel ligands are capable of forming covalent bonds with the metals and/or main group elements that may not be broken under most acidic or basic conditions. The ligands of the present invention are suitable for binding metals and/or main group elements which are in or are capable of being placed in a positive oxidation state, including, but not limited to, yttrium, lanthanum, hafnium, vanadium, chromium, uranium, manganese, iron, cobalt, nickel, palladium, platinum, copper, silver, gold, zinc, cadmium, mercury, lead, tin and the like. The ligands of the present invention are also suitable for binding main group elements which are in or are capable of being placed in a positive oxidation state, hereinafter defined as including gallium, indium, thallium, boron, silicon, germanium, arsenic, antimony, selenium, tellurium, polonium, bismuth, molybdenum, thorium, plutonium and the like.

In one aspect, the present invention relates to chelate ligands consisting of an organic group from which depends at least one alkyl chain that terminates in a sulfur-containing group. The chelate ligands may be of the general formula:

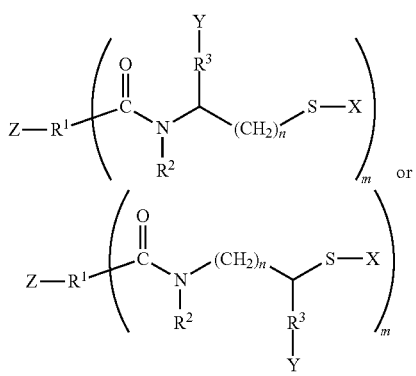

where $R^1$ may be selected from a group comprising organic groups that include, but are not limited to, benzene, pyridine, pyridin-4-one, naphthalene, anthracene, phenanthrene and alkyl groups such as $(CH_2)_y$, where $y=2-8$, $R^2$ may be independently selected from a group comprising hydrogen, alkyls, aryls, a carboxyl group, carboxylate esters, other organic groups that include, but are not limited to, acyls and amides, and biological groups that include, but are not limited to, amino acids and proteins such as cysteine, $R^3$ may be independently selected from a group comprising alkyls, aryls, carboxyl groups, carboxylate esters, other organic groups that include, but are not limited to, acyls and amides, and biological groups that include, but are not limited to, proteins and amino acids such as cysteine, X may be independently selected from a group comprising hydrogen, lithium, sodium, potassium, rubidium, cesium, francium, alkyls, aryls, a carboxyl group, carboxylate esters, cysteine, homocysteine, glutathione, lipoic acid, dihydrolipoic acid, thiophosphate, N-acetyl cysteine, mercaptoacetic acid, mercaptopropionic acid, γ-glutamyl cysteine, phytochelatins, thiosalicylate, organic groups and biological groups, n may independently equal 1-10, m may equal 1-6, Y may be independently selected from a group comprising hydrogen, polymers, silicas and silica supported substrates, and Z may be independently selected from a group comprising hydrogen, alkyls, aryls, a carboxyl group, carboxylate esters, a hydroxyl group, $NH_2$, $HSO_3$, halogens, a carbonyl group, organic groups, biological groups, polymers, silicas and silica supported substrates. In some embodiments n may independently equal to 1-6 or 1-4. In some embodiments m may equal 1-2 or 4-6, and in certain interesting embodiments, m equals 2. In embodiments where m≥2, the sulfur atoms of multiple alkyl chains may share a single X constituent. In such embodiments, X may be independently selected from a group comprising beryllium, magnesium, calcium, strontium, barium and radium.

While not wishing to be bound by any particular theory, it is believed that the stability of the metal and/or main group element complexes formed through utilization of the ligands of the present invention is derived from the multiple interactions between the metal and/or main group element atoms and the sulfur and/or nitrogen atoms on the ligand. Accordingly, it is believed that the sulfur and/or nitrogen atoms form a multidentate bonding arrangement with a metal and/or main group element atom. In embodiments of ligands that include multiple alkyl chains (i.e., m≥2), a metal and/or main group element atom may be bound through interactions with the multiple sulfur and/or nitrogen atoms of the ligand. In embodiments of ligands that include a single alkyl chain (i.e., m=1), a metal and/or main group element atom may be bound through interactions with the sulfur and/or nitrogen atoms of multiple ligands. However, metal and/or main group element atoms may also be bound by the sulfur and/or nitrogen atoms of several ligands that include multiple alkyl chains. Accordingly, the ligands may form metal and/or main group element complexes though the interactions between the metal and/or main group element atoms and the sulfur and/or nitrogen atoms of a single ligand, as well as form polymeric metal and/or main group element complexes through the interactions between the metal and/or main group element atoms and the sulfur and/or nitrogen atoms of multiple ligands.

The compounds may be bonded to supporting material Y at $R^3$. Depending on the value of m, Y may comprise polymers, silicas, silica supported substrates or hydrogen. If m=1, then Y may be selected from a group comprising hydrogen, polymers, silicas and silica supported substrates, alumina and other metal oxide materials. If m>1, then each Y may be independently selected from a group comprising hydrogen, polymers, silicas, silica supported substrates, alumina and other metal oxide materials. Thus, where m>1, the compound may bond to supporting material Y at a single $R^3$, at all of the $R^3$ groups, or any combination thereof. Furthermore, Y may comprise filtration beads or be otherwise embedded or impregnated in a filtration medium. For example, in one embodiment, Y may comprise polystyrene beads such that the sulfur-containing compounds are supported on the polystyrene beads for the filtration of contaminants.

In one useful embodiment, the chelate ligands may be of the general formula:

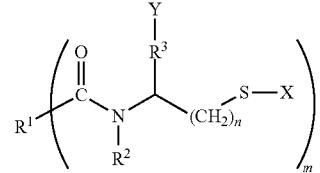

where $R^1$ may be selected from a group comprising benzene, pyridine, naphthalene, anthracene, phenanthrene and alkyl groups, $R^2$ may be independently selected from a group comprising hydrogen, alkyls, aryls, a carboxyl group, carboxylate esters, organic groups and biological groups, $R^3$ may be independently selected from a group comprising alkyls, aryls, a carboxyl group, carboxylate esters, organic groups and biological groups, X may be independently selected from a group comprising hydrogen, lithium, sodium, potassium, rubidium, cesium, francium, cysteine and glutathione, n independently equals 1-10, m=1-6, and Y may be independently selected from a group comprising hydrogen, polymers, silicas and silica supported substrates, with the proviso that when $R^1$ represents an alkyl group, at least one X cannot simultaneously represent hydrogen.

In another useful embodiment, chelate ligands may be of the genera formula:

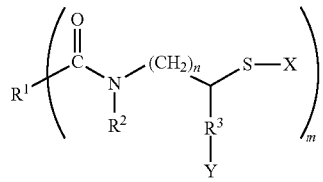

where $R^1$ may be selected from a group comprising benzene, pyridine, naphthalene, anthracene, phenanthrene and alkyl groups, $R^2$ may be independently selected from a group comprising hydrogen, alkyls, aryls, a carboxyl group, carboxylate esters, organic groups and biological groups, $R^3$ may be independently selected from a group comprising alkyls, aryls, a carboxyl group, carboxylate esters, organic groups and biological groups, X may be independently selected from a group comprising hydrogen, lithium, sodium, potassium, rubidium, cesium, francium, cysteine and glutathione, n independently equals 1-10, m=1-6, and Y may be independently selected from a group comprising hydrogen, polymers, silicas and silica supported substrates.

In another useful embodiment, the present invention relates to chelate ligands consisting of an organic structure from which depend two alkyl chains terminating in sulfur-containing groups. The chelate ligands may be of the general formula:

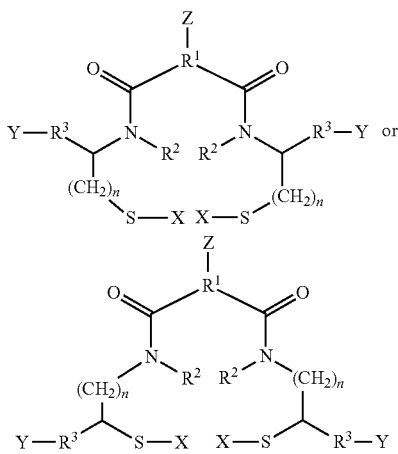

where $R^1$ may be selected from a group comprising benzene, pyridine, pyridin-4-one, naphthalene, anthracene, phenanthrene and alkyl groups, $R^2$ may be independently selected from a group comprising hydrogen, alkyls, aryls, a carboxyl group, carboxylate esters, organic groups and biological groups, $R^3$ may be independently selected from a group comprising alkyls, aryls, a carboxyl group, carboxylate esters, organic groups and biological groups, X may be independently selected from a group comprising hydrogen, lithium, sodium, potassium, rubidium, cesium, francium, cysteine and glutathione, n independently equals 1-10, Y may be independently selected from a group comprising hydrogen, polymers, silicas and silica supported substrates, and Z may be independently selected from a group comprising hydrogen, alkyls, aryls, a carboxyl group, carboxylate esters, a hydroxyl group, $NH_2$, $HSO_3$, halogens, a carbonyl group, organic groups, biological groups, polymers, silicas and silica supported substrates.

In another useful embodiment, the present invention relates to chelate ligands consisting of an organic structure from which depend two alkyl chains terminating in sulfur-containing groups. However, in this embodiment, the two sulfur atoms of the two alkyl chains share one X constituent. The chelate ligands may be of the general formula:

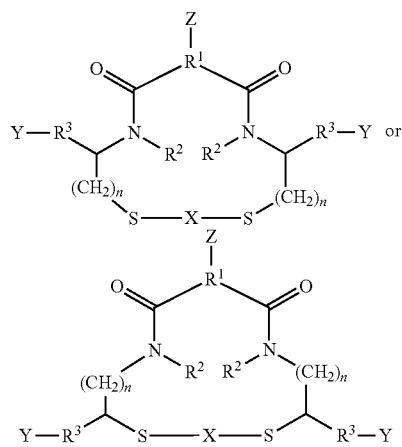

where $R^1$ may be selected from a group comprising benzene, pyridine, pyridin-4-one, naphthalene, anthracene, phenanthrene and alkyl groups, $R^2$ may be independently selected from a group comprising hydrogen, alkyls, aryls, a carboxyl group, carboxylate esters, organic groups and biological groups, $R^3$ may be independently selected from a group comprising alkyls, aryls, a carboxyl group, carboxylate esters, organic groups and biological groups, X may be selected from a group comprising beryllium, magnesium, calcium, strontium, barium and radium, n independently equals 1-10, Y may be independently selected from a group comprising hydrogen, polymers, silicas and silica supported substrates, and Z may be independently selected from a group comprising hydrogen, alkyls, aryls, a carboxyl group, carboxylate esters, a hydroxyl group, $NH_2$, $HSO_3$, halogens, a carbonyl group, organic groups, biological groups, polymers, silicas and silica supported substrates.

In another useful embodiment, the present invention relates to chelate ligands consisting of a ring structure from which depend two alkyl chains terminating in sulfur-containing groups. The chelate ligands may be of the general formula:

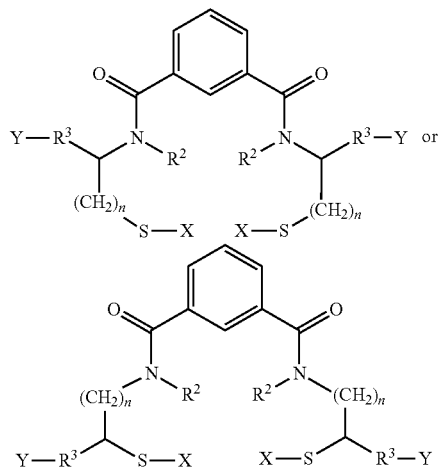

where $R^2$ may be independently selected from a group comprising hydrogen, alkyls, aryls, a carboxyl group, carboxylate esters, organic groups and biological groups, $R^3$ may be independently selected from a group comprising alkyls, aryls, a carboxyl group, carboxylate esters, organic groups and biological groups, X may be independently selected from a group comprising hydrogen, lithium, sodium, potassium, rubidium, cesium, francium, cysteine and glutathione, n independently equals 1-10, and Y may be independently selected from a group comprising hydrogen, polymers, silicas and silica supported substrates. As disclosed in U.S. Pat. No. 6,586,600, chelate ligands of the above general formula, wherein the $R^3$ groups (as well as the $R^2$ groups) comprise hydrogen, both n equal 1, and both Y comprise hydrogen, may be referred to as "B9."

In another useful embodiment of B9, the chelate ligands are of the formula:

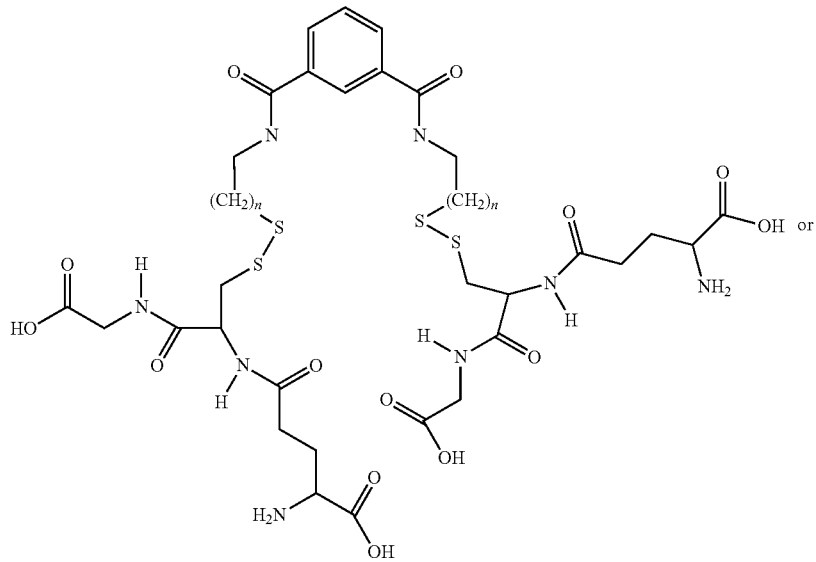

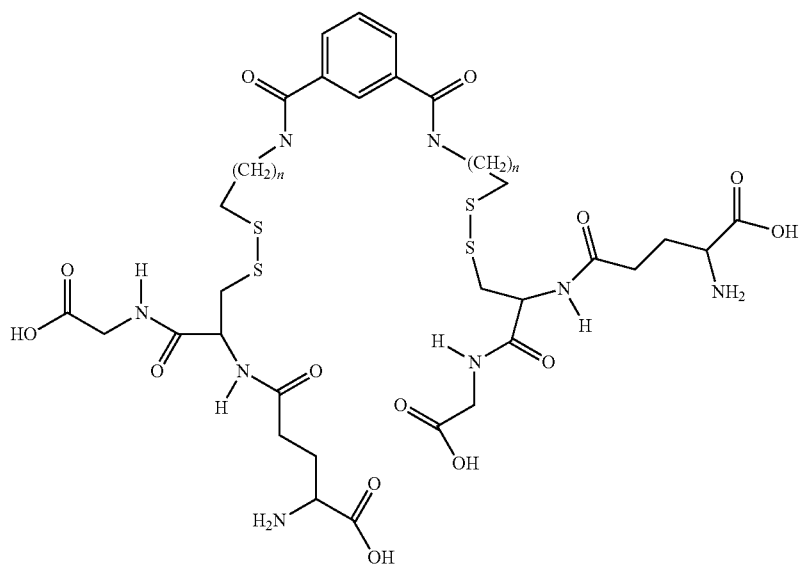

where n independently equals 1-10. Chelate ligands of this general formula may be referred to as "glutathione B9" or abbreviated to "GB9."

In one useful embodiment of GB9, the chelate ligand is of the formula:

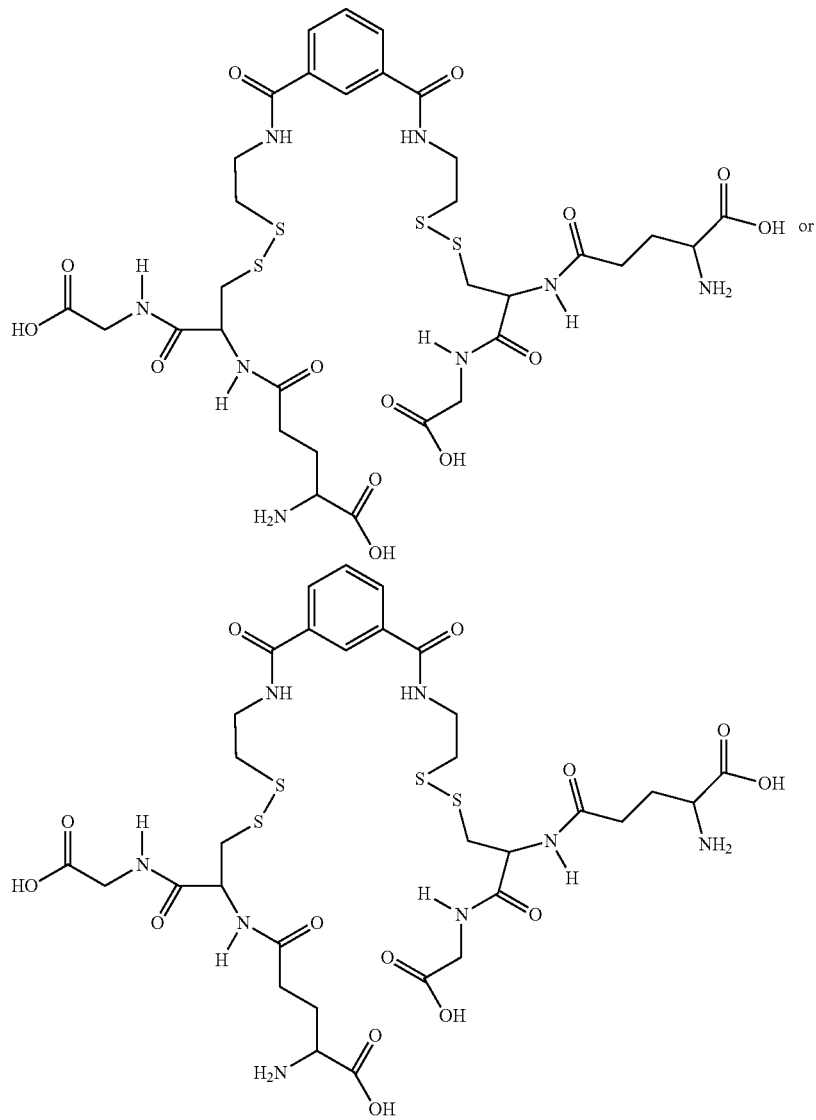

In another useful embodiment, the present invention relates to chelate ligands consisting of a ring structure from which depend two alkyl chains terminating in sulfur-containing groups. In this embodiment the two sulfur atoms of the two alkyl chains share one X group. The chelate ligands may be of the general formula:

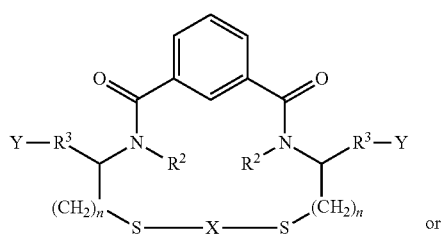

or

-continued

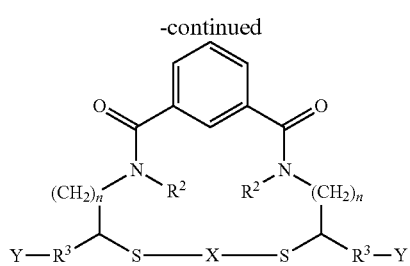

where $R^2$ may be independently selected from a group comprising hydrogen, alkyls, aryls, a carboxyl group, carboxylate esters, organic groups and biological groups, $R^3$ may be independently selected from a group comprising alkyls, aryls, a carboxyl group, carboxylate esters, organic groups and biological groups, X may be selected from a group comprising beryllium, magnesium, calcium, strontium, barium and radium, n independently equals 1-10, and Y may be independently selected from a group comprising hydrogen, polymers, silicas and silica supported substrates.

In another useful embodiment, the chelate ligands are of the formula:

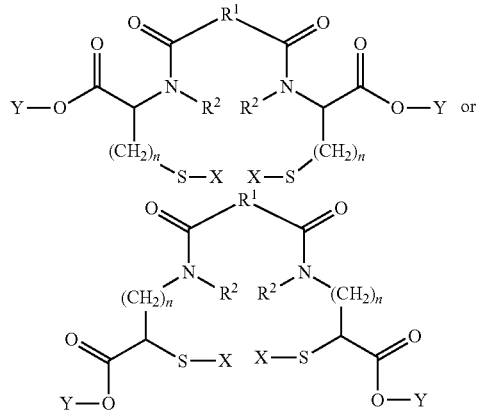

where $R^1$ may be selected from a group comprising benzene, pyridine, naphthalene, anthracene, phenanthrene and alkyl groups, $R^2$ may be independently selected from a group comprising alkyls, aryls, a carboxyl group, carboxylate esters, organic groups and biological groups, X may be independently selected from a group comprising hydrogen, lithium, sodium, potassium, rubidium, cesium, francium, cysteine, and glutathione, n independently equals 1-10, and Y may be independently selected from a group comprising hydrogen, polymers, silicas and silica supported substrates. Chelate ligands of these general formulas may be referred to as "acid B9" or abbreviated to "AB9."

In one useful embodiment of AB9, the chelate ligands are of the formula:

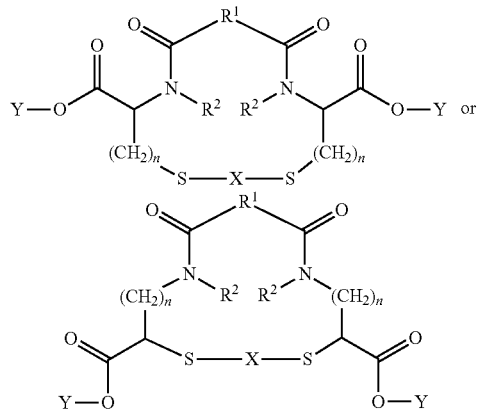

where $R^1$ may be selected from a group comprising benzene, pyridine, naphthalene, anthracene, phenanthrene and alkyl groups, $R^2$ may be independently selected from a group comprising hydrogen, alkyls, aryls, a carboxyl group, carboxylate esters, organic groups and biological groups, X may be independently selected from a group comprising beryllium, magnesium, calcium, strontium, barium and radium, n independently equals 1-10, and Y may be independently selected from a group comprising hydrogen, polymers, silicas and silica supported substrates.

In another useful embodiment of AB9, the chelate ligands are of the formula:

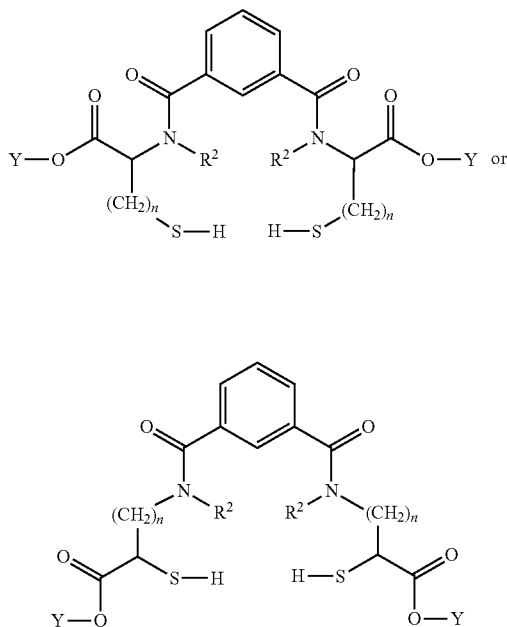

where $R^2$ may be independently selected from a group comprising hydrogen, alkyls, aryls, a carboxyl group, carboxylate esters, organic groups and biological groups, n independently equals 1-10, and Y may be independently selected from a group comprising hydrogen, polymers, silicas and silica supported substrates.

In another useful embodiment of AB9, the chelate ligands are of the formula:

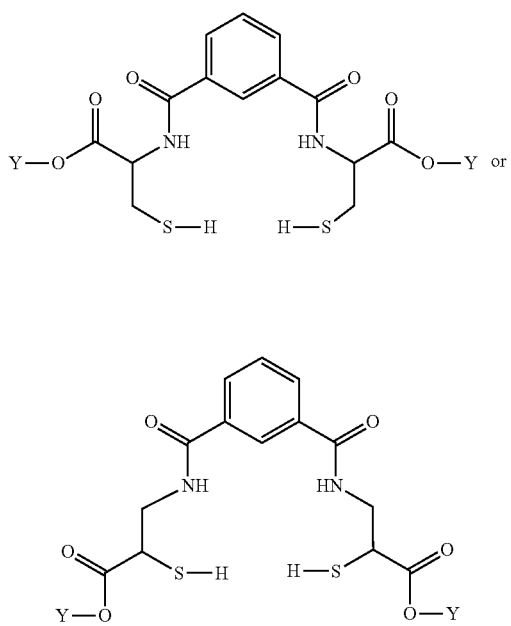

where Y may be independently selected from a group comprising hydrogen, polymers, silicas and silica supported substrates.

In another useful embodiment of AB9, the chelate ligands are of the formula:

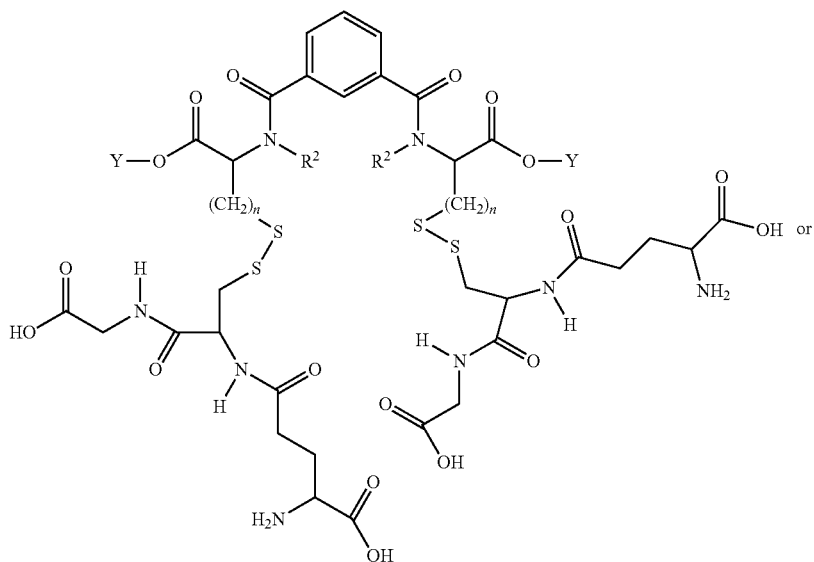

or

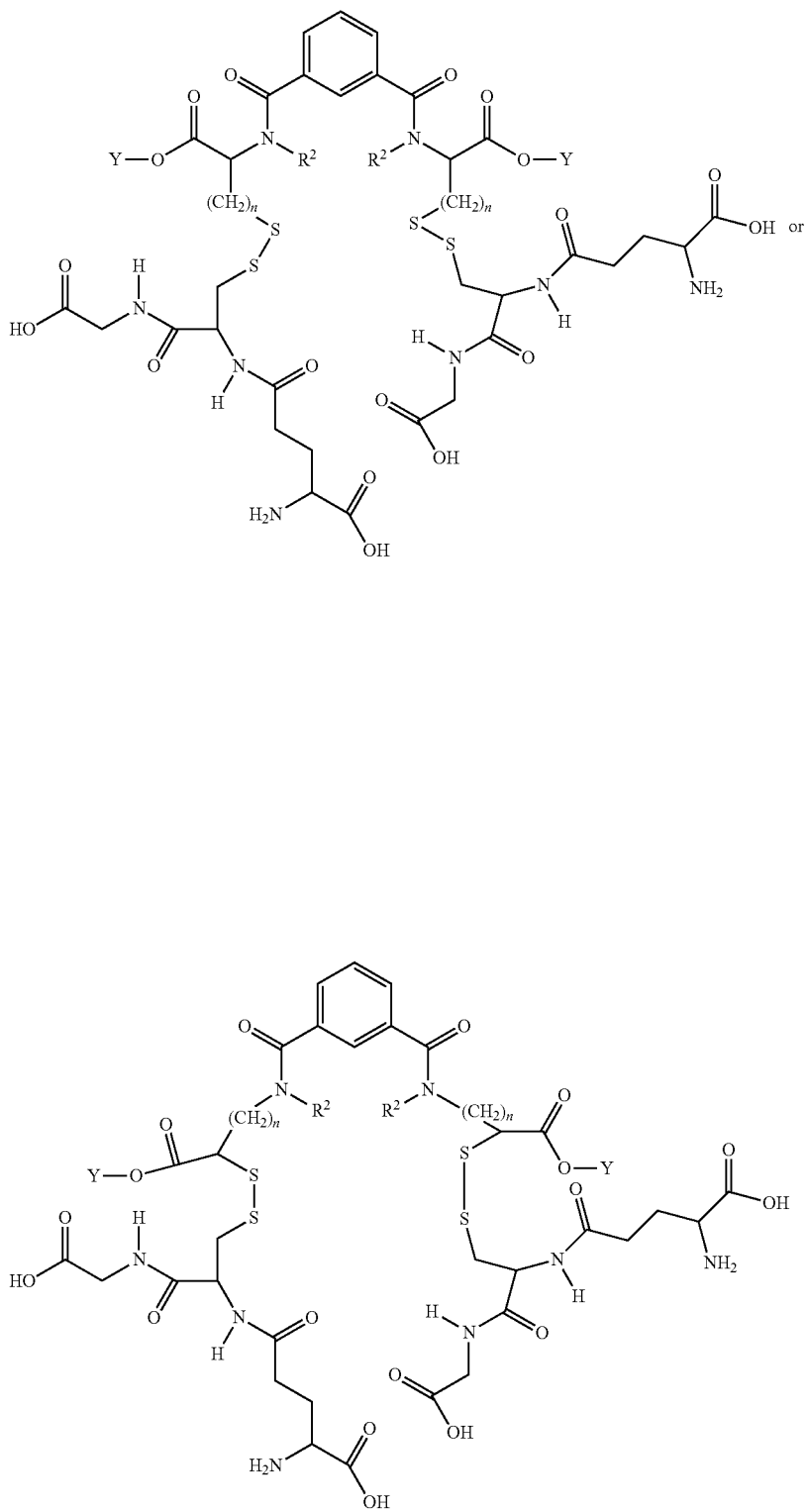

where $R^2$ may be independently selected from a group comprising hydrogen, alkyls, aryls, a carboxyl group, carboxylate esters, organic groups and biological groups, n independently equals 1-10, and Y may be independently selected from a group comprising hydrogen, polymers, silicas and silica supported substrates. Chelate ligands of this general formula may be referred to as "glutathione AB9" or abbreviated to "GAB9."

In one useful embodiment of GAB9, the chelate ligand is of the formula:

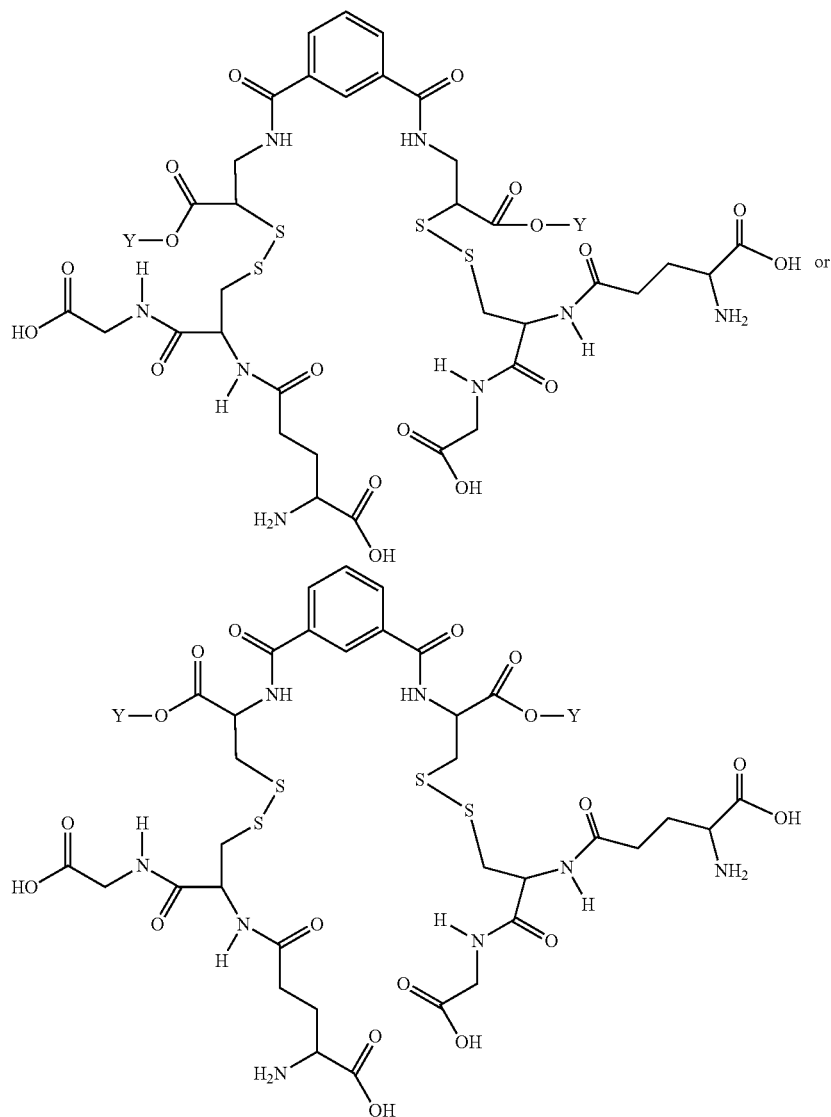

where Y may be independently selected from a group comprising hydrogen, polymers, silicas and silica supported substrates.

In another useful embodiment of AB9, the AB9 may be material supported with a structure of:

where PS may be polystyrene or a co-polymer containing polystyrene. In one even more particular embodiment, PS may be chloromethylated polystyrene-co-divinylbenzene (2% DVB, 200-400 mesh).

In one particular embodiment of the material supported AB9, the material may be derivatized prior to the addition of AB9, or its equivalent, providing a structure with the formula:

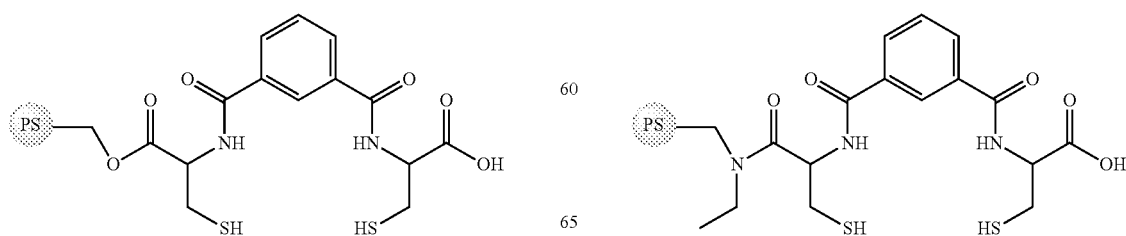

Alternatively, AB9 may be loaded onto amine functionalized silica (Silica-NH$_2$). In one exemplary embodiment, Silica-NH$_2$, produced by binding γ-aminopropyltriethoxysilane on silica-60 (Si60), may be refluxed in a solution of AB9 in ethanol producing a structure of the formula:

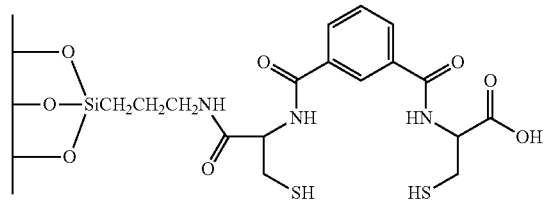

In an alternative preparation, SiNH$_2$ may be treated with AB9 in the presence of dicyclohexylcarbodiimide (DCC) to facilitate the coupling of the AB9 to the amine of the PS.

In another useful embodiment, the chelate ligands are of the formula:

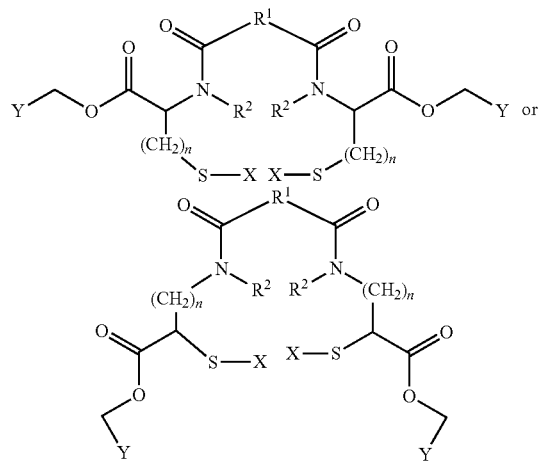

where R$^1$ may be selected from a group comprising benzene, pyridine, naphthalene, anthracene, phenanthrene and alkyl groups, R$^2$ may be independently selected from a group comprising hydrogen, alkyls, aryls, a carboxyl group, carboxylate esters, organic groups and biological groups. X may be independently selected from a group comprising hydrogen, lithium, sodium, potassium, rubidium, cesium, francium, cysteine and glutathione, n independently equals 1-10, and Y is a methyl group. Chelate ligands of these general formulas may be referred to as "methyl ester AB9" or abbreviated to "MEAB9."

In one useful embodiment of MEAB9, the chelate ligands are of the formula:

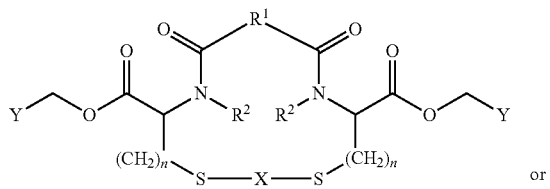

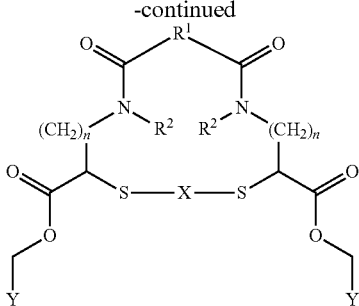

where R$^1$ may be selected from a group comprising benzene, pyridine, naphthalene, anthracene, phenanthrene and alkyl groups, R$^2$ may be independently selected from a group comprising hydrogen, alkyls, aryls, a carboxyl group, carboxylate esters, organic groups and biological groups, X may be independently selected from a group comprising beryllium, magnesium, calcium, strontium, barium and radium, n independently equals 1-10, and Y is a methyl group.

In another useful embodiment of MEAB9, the chelate ligands are of the formula:

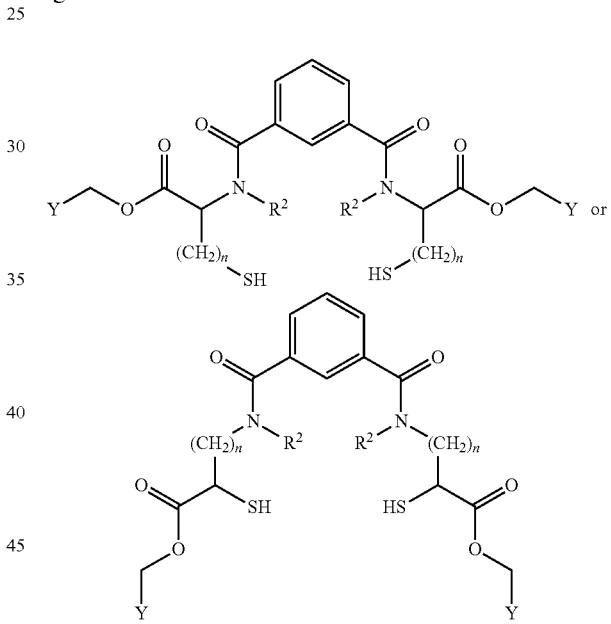

where R$^2$ may be independently selected from a group comprising hydrogen, alkyls, aryls, a carboxyl group, carboxylate esters, organic groups and biological groups, n independently equals 1-10, and Y is a methyl group.

In another useful embodiment of MEAB9, the chelate ligands are of the formula:

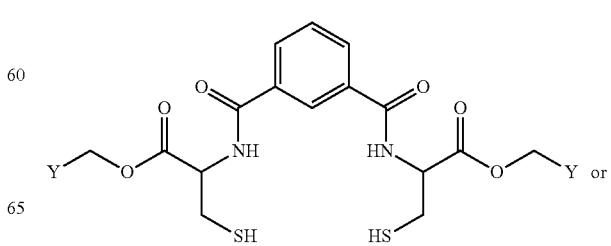

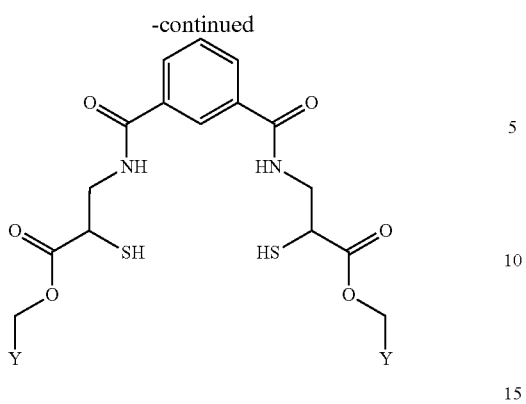
where Y is a methyl group,
In another useful embodiment of MEAB9, the chelate ligands are of the formula:
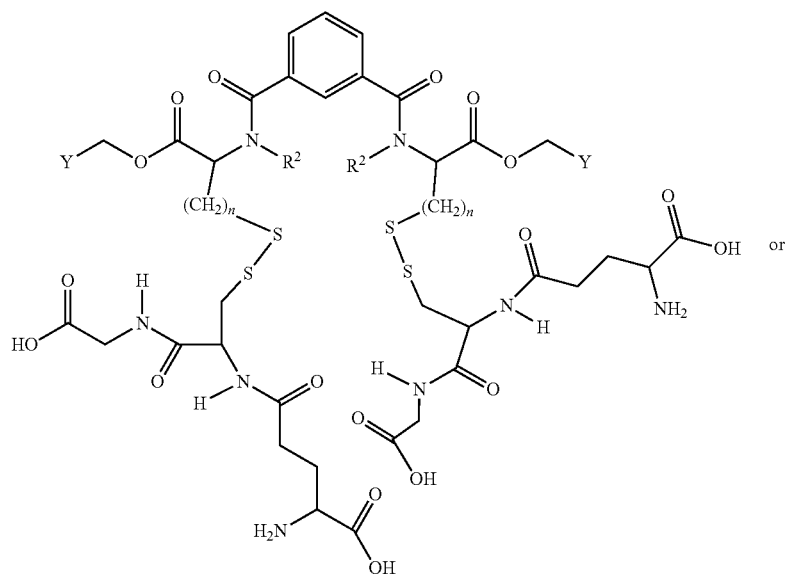
or
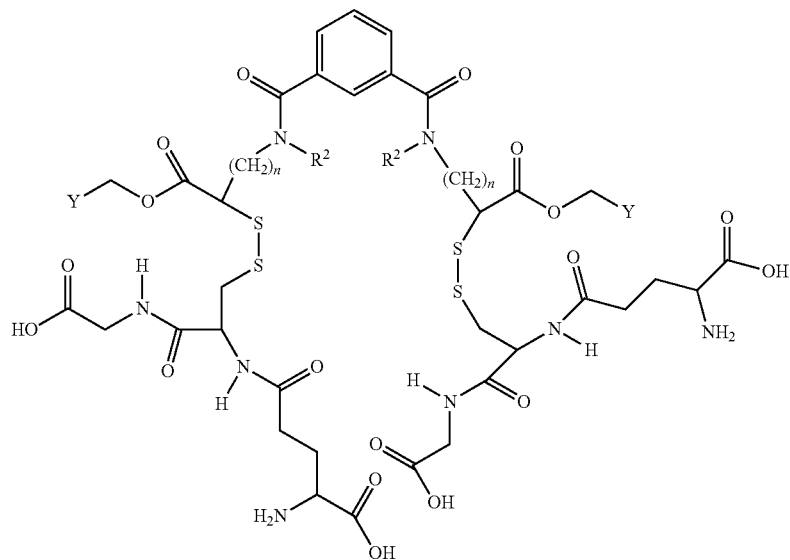

where R² may be independently selected from a group comprising hydrogen, alkyls, aryls, a carboxyl group, carboxylate esters, organic groups and biological groups, n independently equals 1-10, and Y is a methyl group. Chelate ligands of this general formula may be referred to as "glutathione methyl ester AB9" or abbreviated to "GMEAB9."

In one useful embodiment of GMEAB9, the chelate ligands are of the formula:

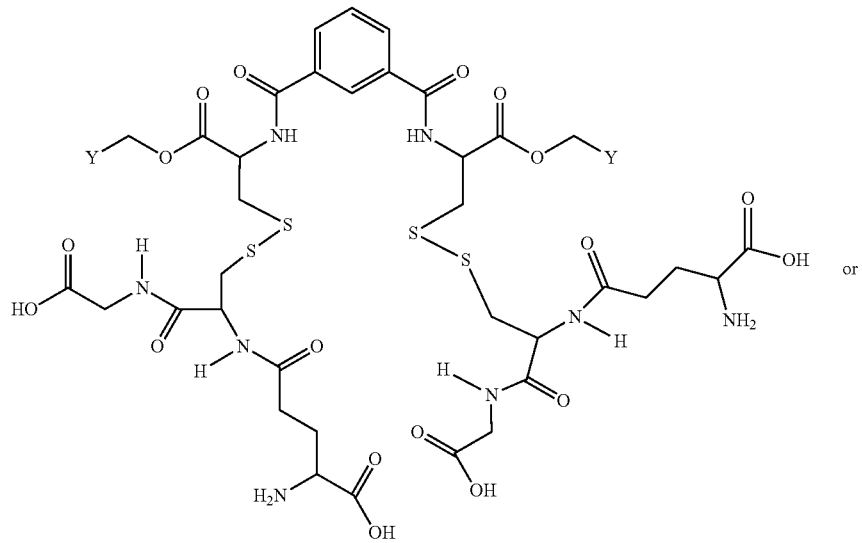

or

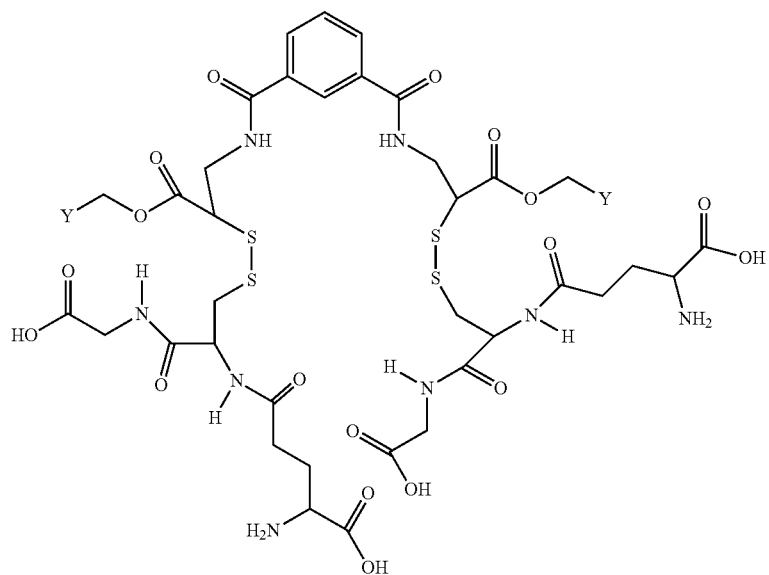

where Y is a methyl group.

In another useful embodiment, the chelate ligands are of the formula:

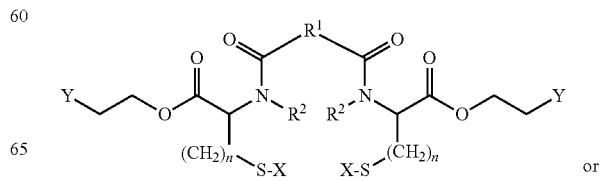

or

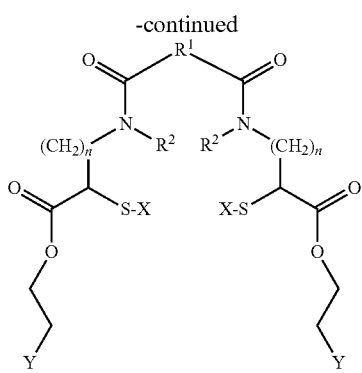

where $R^1$ may be selected from a group comprising benzene, pyridine, naphthalene, anthracene, phenanthrene and alkyl groups, $R^2$ may be independently selected from a group comprising hydrogen, alkyls, aryls, a carboxyl group, carboxylate esters, organic groups and biological groups, X may be independently selected from a group comprising hydrogen, lithium, sodium, potassium, rubidium, cesium, francium, cysteine and glutathione, n independently equals 1-10, and Y is an ethyl group. Chelate ligands of this general formula may be referred to as "ethyl ester AB9" or abbreviated to "EEAB9."

In one useful embodiment of EEAB9, the chelate ligands are of the formula:

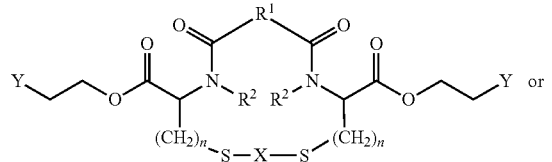 or

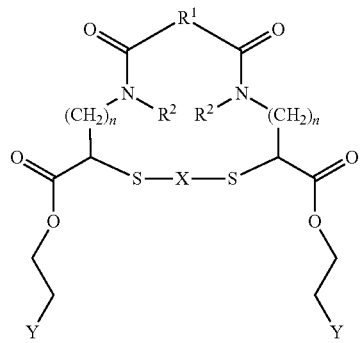

where $R^1$ may be selected from a group comprising benzene, pyridine, naphthalene, anthracene, phenanthrene and alkyl groups, $R^2$ may be independently selected from a group comprising hydrogen, alkyls, aryls, a carboxyl group, carboxylate esters, organic groups and biological groups, X may be independently selected from a group comprising beryllium, magnesium, calcium, strontium, barium and radium, n independently equals 1-10, and Y is an ethyl group.

In another useful embodiment of EEAB9, the chelate ligands are of the formula:

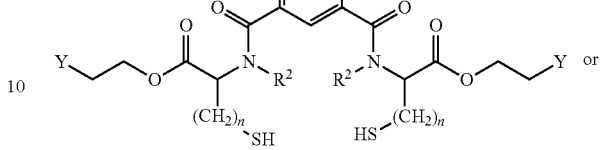 or

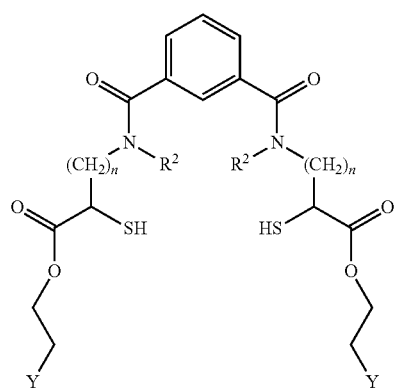

where $R^2$ may be independently selected from a group comprising hydrogen, alkyls, aryls, a carboxyl group, carboxylate esters, organic groups and biological groups, n independently equals 1-10, and Y is an ethyl group.

In another useful embodiment of EEAB9, the chelate ligands are of the formula:

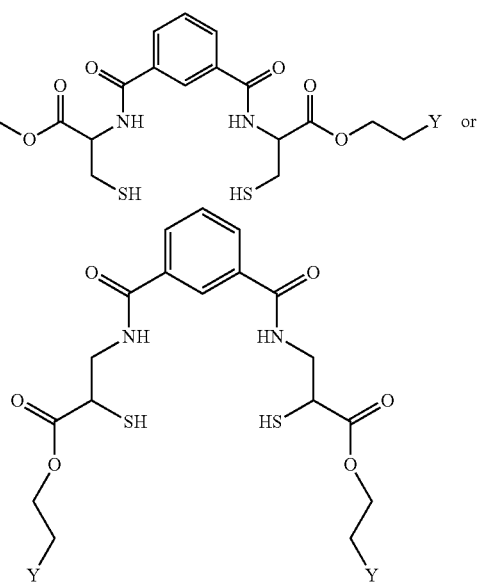

where Y is an ethyl group.

In another useful embodiment of EEAB9, the chelate ligands are of the formula:

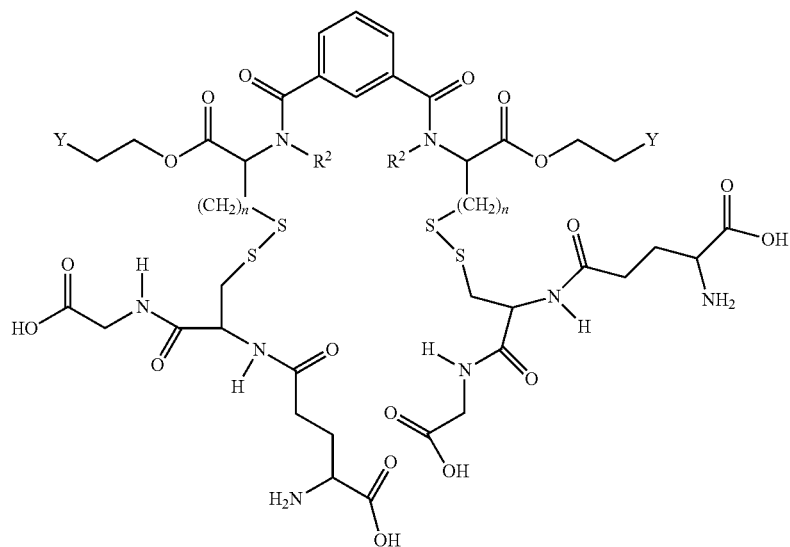

or

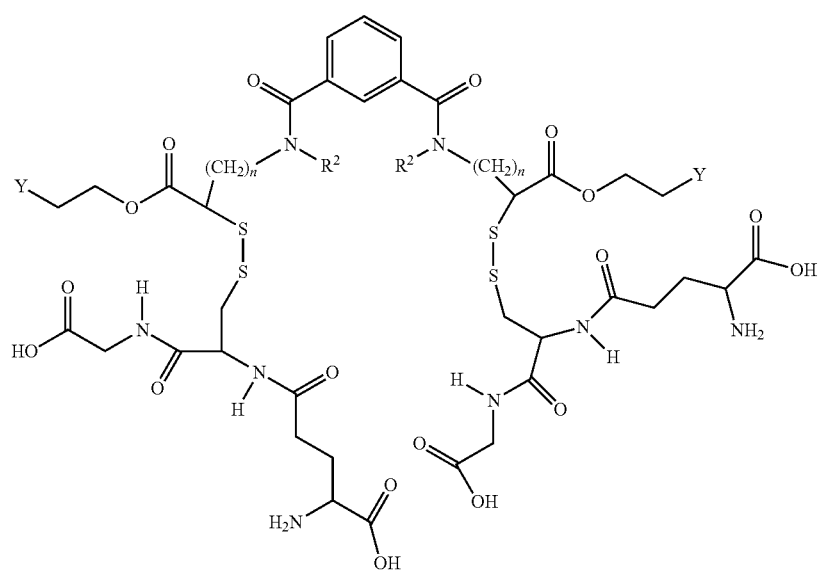

where $R^2$ may be independently selected from a group comprising hydrogen, alkyls, aryls, a carboxyl group, carboxylate esters, organic groups and biological groups, n independently equals 1-10, and Y is an ethyl group. Chelate ligands of this general formula may be referred to as "glutathione ethyl ester AB9" or abbreviated to "GEEAB9."

In one useful embodiment of GEEAB9, the chelate ligands are of the formula:

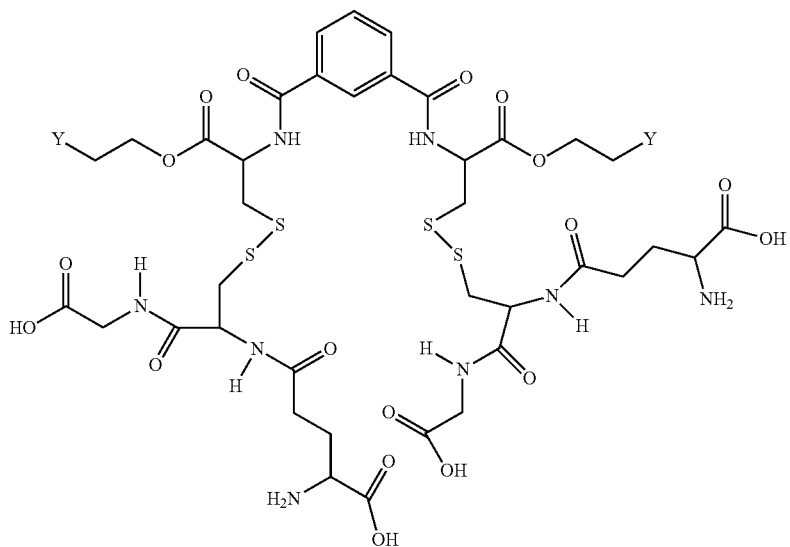

or

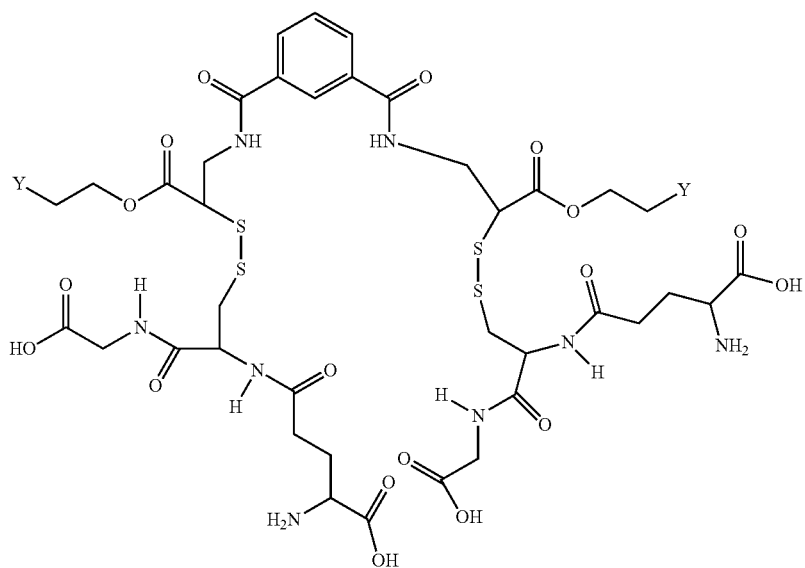

where Y is an ethyl group.

In another useful embodiment, the chelate ligands are of the formula:

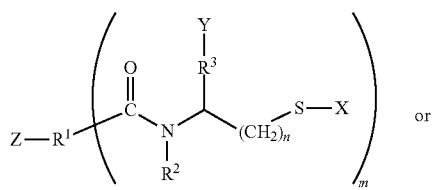

or

-continued

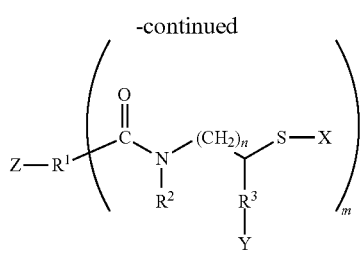

where $R^1$ is selected from a group including benzene, pyridine, pyridin-4-one, naphthalene, anthracene, phenanthrene and alkyl groups, $R^2$ is independently selected from a group including hydrogen, alkyls, aryls, a carboxyl group, carboxylate esters, organic groups and biological groups, $R^3$ is independently selected from a group including alkyls, aryls, a carboxyl group, carboxylate esters, organic groups and biological groups, X is independently selected from a group including hydrogen, lithium, sodium, potassium, rubidium, cesium, francium, beryllium, magnesium, calcium, strontium, barium, radium, alkyls, aryls, a carboxyl group, carboxylate esters, cysteine, homocysteine, glutathione, lipoic acid, dihydrolipoic acid, thiophosphate, N-acetyl cysteine, mercaptoacetic acid, mercaptopropionic acid, γ-glutamyl cysteine, phytochelatins, thiolsalicylate, organic groups and biological groups, n independently equals 1-10, m=1-6, Y is independently selected from a group including hydrogen, polymers, silicas and silica supported substrates, and Z is selected from a group including hydrogen, alkyls, aryls, a carboxyl group, carboxylate esters, a hydroxyl group, $NH_2$, $HSO_3$, halogens, a carbonyl group, organic groups, biological groups, polymers, silicas and silica supported substrates.

One exemplary compound comprises $R^1$=benzene, $R^2$=hydrogen, $R^3$=hydrogen, m=2, n=1, X=an acetyl group, Y=hydrogen, and Z=a hydroxyl group as is shown below:

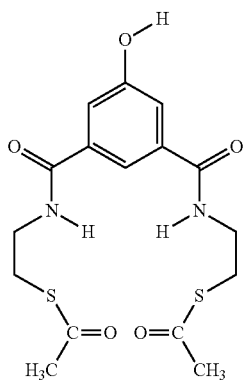 [SMILES: CC(=O)SCCNC(=O)c1cc(O)cc(C(=O)NCCSC(C)=O)c1]

Another exemplary compound comprises $R^1$=benzene, $R^2$=hydrogen, $R^3$=hydrogen, m=2, n=1, X=hydrogen, Y=hydrogen, and Z=a hydroxyl group as is shown below:

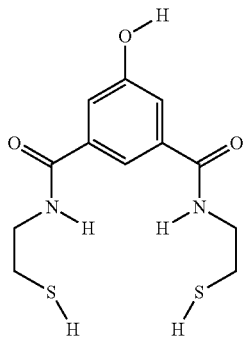 [SMILES: O=C(NCCS)c1cc(O)cc(C(=O)NCCS)c1]

Another exemplary compound comprises $R^1$=pyridin-4-one, $R^2$=hydrogen, $R^3$=hydrogen, m=2, n=1, X=hydrogen, Y=hydrogen, and Z=a hydroxyl group as is shown below:

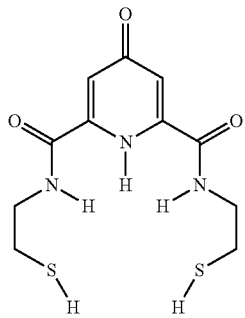 [SMILES: O=C(NCCS)c1cc(=O)cc(C(=O)NCCS)[nH]1]

Within the scope of the present disclosure, other new compounds can be prepared having different combinations of Z, Y, n and X groups. For example, one exemplary compound utilizing cysteine in the synthetic procedure can comprise $R^1$=benzene, $R^2$=hydrogen, $R^3$=a carboxyl group, m=2, n=1, X=hydrogen, Y=hydrogen, and Z=a hydroxyl group as is shown below:

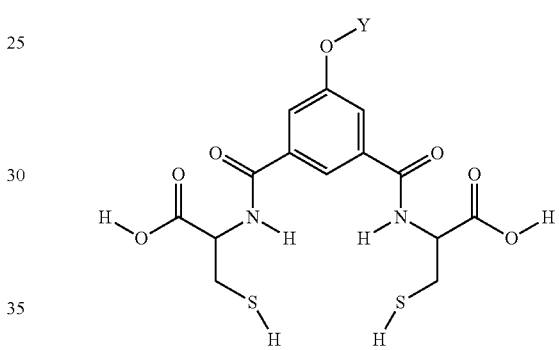

As will be appreciated by one skilled in the art, it is possible to utilize aromatic groups other than benzene and pyridine for the introduction of the thiol and thiolate groups. For example, naphthalene, anthracene, phenanthrene, etc. can be used. For example, one such exemplary compound can comprise $R^1$=naphthalene, $R^2$=hydrogen, $R^3$=hydrogen, m=2, n=1, X=hydrogen, Y=hydrogen, and Z=hydroxyl groups:

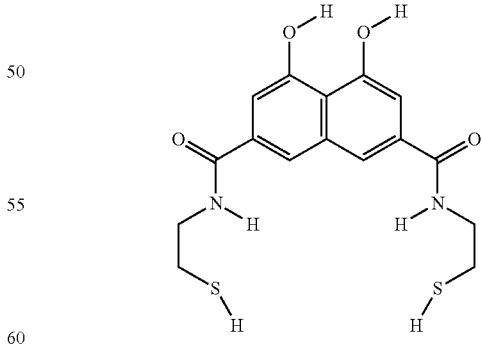

Accordingly, the novel ligands of the present invention may also be adapted to a variety of environmental situations requiring binding and/or removal of metals and/or main group elements, such as, for example, additives in flue gas desulphurization (FGD) scrubbers to remove metals and/or main group elements from coal-fired power plant emissions, treatment of industrial waste water, treatment of acid mine drainage, soil remediation, and the like. As will be appreciated by those skilled in the art, the chelate ligands of the present invention may be utilized alone or in varying combinations to achieve the objects of the present invention.

In one aspect, the present disclosure relates to a method of removing metals and/or main group elements from a starting material. The method of the present invention comprises contacting a starting material (gas, liquid or solid) with an effective amount of a novel sulfur-containing chelate ligand as described above for a sufficient time to form at least one stable ligand-metal and/or ligand-main group element complex(es). The ligand-metal and/or ligand-main group element complex(es) may remain stable through a range of acidic and basic pH values. In other words, the ligand-metal and/or ligand-main group element complex(es) do not release appreciable amounts of the contaminant element(s) through a range of acidic and basic pH values. For example, the B9-Hg complex precipitate does not release appreciable amounts of mercury within a pH range from about 1 to about 13. However, generally, ligand-metal and/or ligand-main group element complex(es) do not release appreciable amounts of the contaminant elements within a pH range from about 6 to about 8.

In another aspect, the present disclosure relates to a method of treating water, such as surface, ground, or waste water, containing metals and/or main group elements, comprising admixing said water with an effective amount of the sulfur-containing chelate ligand as described above for a sufficient time to form at least one stable ligand-metal and/or ligand-main group element complex(es), and separating said complex(es) from said water.

In still another aspect, the present disclosure relates to a method of treating aqueous acid mine drainage or water from actual mining processes containing soft heavy metals and/or main group elements, comprising admixing said acid mine drainage or water from actual mining processes with an effective amount of the sulfur-containing, chelate ligand as described above for a sufficient time to form at least one stable ligand-metal and/or ligand-main group element complex(es), and separating said complex(es) from said acid mine drainage.

In still another aspect, the present disclosure relates to a method of remediation of soil containing, soft heavy metals and/or main group elements, comprising admixing said soil with an effective amount of the sulfur-containing chelate ligand as described above for a sufficient time to form at least one stable ligand-metal and/or ligand-main group element complex(es). The soil so treated may then be left in situ or removed for disposal without concerns regarding, leaching of said metals and/or main group elements into the environment.

In yet another aspect, the present disclosure relates to a method of treating a gas, such as an emissions gas from a power plant containing soft heavy metals and/or main group elements, comprising passing said gas through a filter utilizing an effective amount of the sulfur-containing chelate ligand as described above to form at least one stable ligand-metal and/or ligand-main group complex(es), therefore filtering said complex from said gas.

In yet another aspect, the present disclosure relates to a method of therapeutically treating a human and/or animal with the sulfur-containing chelate ligands described above, to methods for altering the hydrophobicity or hydrophilicity of such chelators in order to tailor the tissue to which the chelators partition, and to various chelate ligands synthesized to accomplish those methods. The chelators find use in binding and clearance of a variety of heavy metals and/or main group elements, including without limitation mercury, lead, arsenic, cadmium, tin, bismuth, indium, nickel, copper, thallium, gold, silver, platinum, uranium, iron, molybdenum, thorium, polonium, plutonium, antimony, and the like.

Broadly, the method comprises selecting chelate ligands as described herein and modifying the ligands to the desired state of hydrophilicity or hydrophobicity in accordance with the tissue into which the chelator is desired to partition. Still further, the method described herein contemplates modifying such chelators such that an initially hydrophilic chelator derivative is rendered hydrophobic after administration, to more effectively partition into intracellular areas and lipid-containing tissues. Even further, it is contemplated to provide a chelator derivative which is initially hydrophobic for partitioning into lipid-containing tissues for clearance via a fecal route, and after such partitioning is rendered hydrophilic for clearance via the kidney.

Still yet further, it is contemplated to provide uncharged, ester-containing chelate ligands which are initially hydrophilic, to allow uniform delivery throughout the body such as by an intravenous route. After delivery, the chelator is reduced to a hydrophobic condition for partitioning into lipid-containing areas. Following intracellular localization, the hydrophobic chelate ligand is converted again to a hydrophilic state. It will be appreciated that this latter aspect provides a chelate ligand which is uniformly deliverable throughout the body (such as by IV procedures), which partitions into lipid-containing areas where heavy metals concentrate, and which is available for clearance via both kidney and the fecal route. This is similar in function to the method of action of, for example, P450 detoxifying enzymes, which oxidize hydrophobic, uncharged organic molecules which are then converted to water soluble forms by addition of water soluble compounds (e.g. glutathione, sulfate) for removal through naturally designed systems.

In one embodiment of the described method, a chelate ligand such as those described above may be coupled to a charged molecule having a terminal sulfhydryl group to provide a hydrophilic derivative for delivery. After distribution of the derivative, such as by intravenous delivery, the derivative reverts to the hydrophilic form via a reductive process in the bloodstream, releasing the original hydrophobic chelate ligand and the previously coupled charged molecule. In particular embodiments of this aspect, the charged molecule is coupled to the starting chelate ligand compound via disulfide bonds, which are readily reduced in the body to release the charged molecule and the hydrophobic chelate ligand which then partitions into lipid-containing tissue. Such charged compounds should be non-toxic, natural compounds having a free thiol group.

Once in the microenvironment of the tissue, the hydrophobic chelate ligand partitions into lipid-containing tissues, existing in close proximity to a majority of the body burden of heavy metals and thereby improving the effectiveness of the chelator by such proximity. A variety of natural and synthetic charged molecules including terminal sulfhydryl groups are contemplated herein (e.g., glutathione, cysteine, homocysteine, lipoic acid, dihydrolipoic acid, thiophosphate, N-acetyl cysteine, mercaptoacetic acid, mercaptopropionic acid, γ-glutamyl cysteine, phytochelatins and thiolsalicylate).

In the microenvironment of the cells or tissues, cellular esterases hydrolyze the uncharged ester groups into charged carboxylic acids. This conversion renders the chelators hydrophilic, and excretable via the kidney in a rapid manner. Because the chelate ligands described herein are true chelators rather than mere binders, excretion via a kidney route does not carry the risk of release of bound metal in the kidney as is the case for currently approved metal binders used in other methods of chelation therapy.

The compositions and methods of the present invention may be accomplished by various means which are illustrated in the examples below. These examples are intended to be illustrative only, as numerous modifications and variations will be apparent to those skilled in the art. Examples 1-8 are directed to embodiments of the above-detailed chelate ligands, and Examples 9-18 are directed to embodiments of the above-detailed chelate ligands that are material supported.

EXAMPLE 1

This example details the synthesis of one non-limiting embodiment of AB9 by the following scheme:

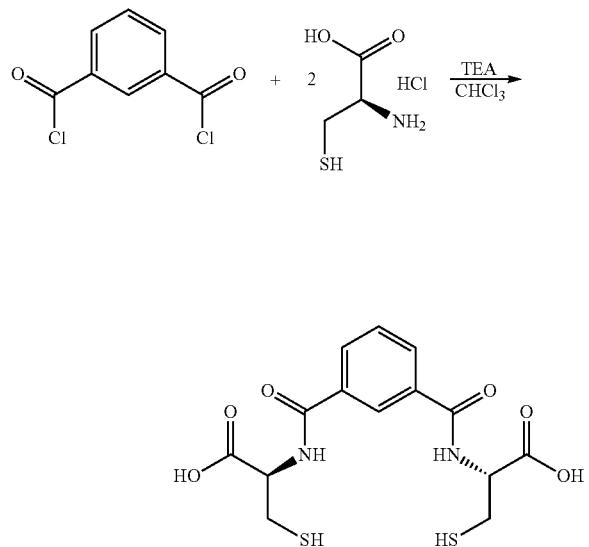

0.78 grams of L-cysteine hydrochloride (5.0 mmol) obtained from Sigma-Aldrich® was dissolved in 100 mL deionized water. 1.02 grams of triethylamine (10 mmol; 1.4 mL), hereinafter referred to as "TEA," and 0.5 grams of isophthaloyl chloride (2.5 mmol) obtained from TCI® were each dissolved separately in 20 mL of tetrahydrofuran, hereinafter referred to as "THF," obtained from Acros Organics®. The TEA dissolved in THF was slowly added to the solution of L-cysteine hydrochloride in deionized water, which was stirring in a flask under a flow of $N_2$ gas. After stirring for 5-10 minutes, the isophthaloyl chloride dissolved in THF was slowly added to the flask. As the reaction proceeded, the color of the reaction mixture turned to light yellow. The reaction mixture continued stirring for 16-18 hours. At the end of the 16-18 hours, the aqueous layer was extracted utilizing 100 mL of ethyl acetate. The ethyl acetate layer was then dried over sodium sulfate, filtered, and evacuated to dryness. The product was recovered as a light yellow solid. The product was soluble in $CHCl_3$, acetone, ethanol and water.

EXAMPLE 2

This example details the synthesis of one non-limiting embodiment of MEAB9 by the following scheme:

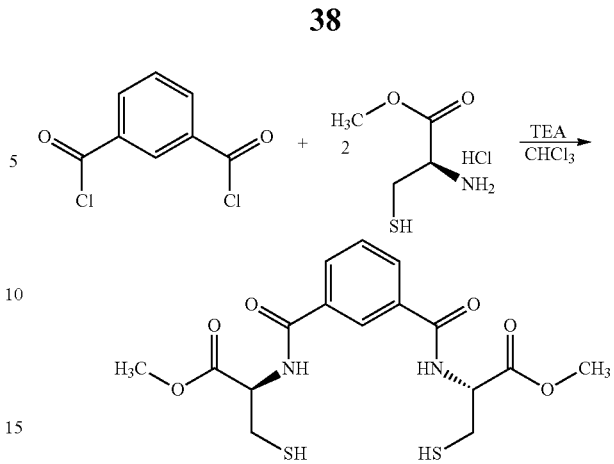

2.57 grams of L-cysteine methyl ester hydrochloride (15 mmol) was dissolved in 150 mL of $CHCl_3$. 1.52 grams of TEA (15 mmol; 2.07 mL) was dissolved in 25 mL of $CHCl_3$. 1.0 gram of isophthaloyl chloride (5 mmol) was dissolved in 40 mL of $CHCl_3$. The TEA solution and the isophthaloyl chloride solution were slowly added to the L-cysteine methyl ester hydrochloride solution. The reaction was stirred for 24 hours. The reaction solution was then filtered and the filtrate was washed three times with 200 mL of 10% Omnitrace® hydrochloric acid. After washing, the $CHCl_3$ layer was filtered again and dried over anhydrous $Na^2SO_4$. The $CHCl_3$ was then removed under vacuum and the product was obtained as a highly viscous oily liquid. The oily liquid was dissolved again in $CHCl_3$ and the $CHCl_3$ was subsequently removed under vacuum. This process was repeated twice and the resulting white solid was then washed twice with diethyl ether. The remaining solvent was removed and the solid was dried under vacuum. The product was recovered as a white solid. The product was soluble in $CHCl_3$, acetone, ethanol and water.

EXAMPLE 3

This example details the synthesis of one non-limiting embodiment of EEAB9 by the following scheme:

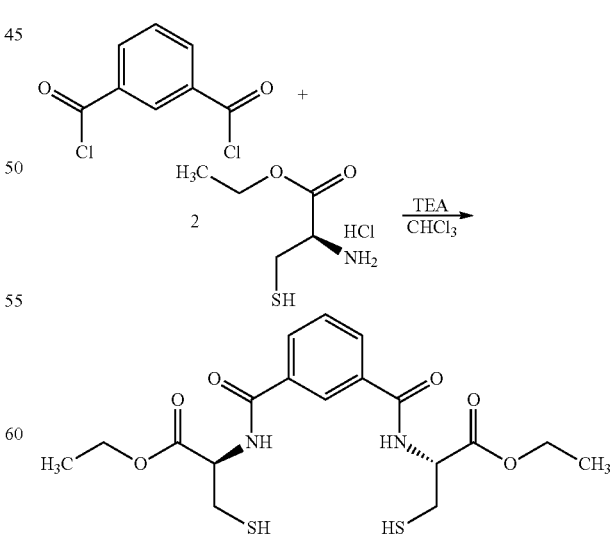

2.72 grams of L-Cysteine ethyl ester hydrochloride (15 mmol) was dissolved in 150 mL of $CHCl_3$. 1.48 grams of TEA (15 mmol; 2.02 mL) was dissolved in 25 mL of CHCl₃, 1 gram of isophthaloyl chloride (5 mmol) was dissolved in 40 mL of CHCl₃. The TEA solution and the isophthaloyl chloride solution were slowly added to the L-cysteine ethyl ester hydrochloride solution. The reaction was stirred for 24 hours. The reaction solution was then filtered and the filtrate was washed with 1.5 L of 20% Omnitrace® hydrochloric acid. After washing, the CHCl₃ layer was filtered again and dried over anhydrous Na₂SO₄. The CHCl₃ was then removed under vacuum and the product was obtained as a highly viscous oily liquid. The oily liquid was dissolved again in CHCl₃ and the CHCl₃ was subsequently removed under vacuum. This process was repeated twice and the resulting white solid was then washed twice with diethyl ether. The remaining solvent was removed and dried under vacuum. The product was recovered as a white solid. The product was soluble in CHCl₃, acetone, ethanol and water.

EXAMPLE 4

This example details the synthesis of one non-limiting embodiment of GB9 by the following scheme:

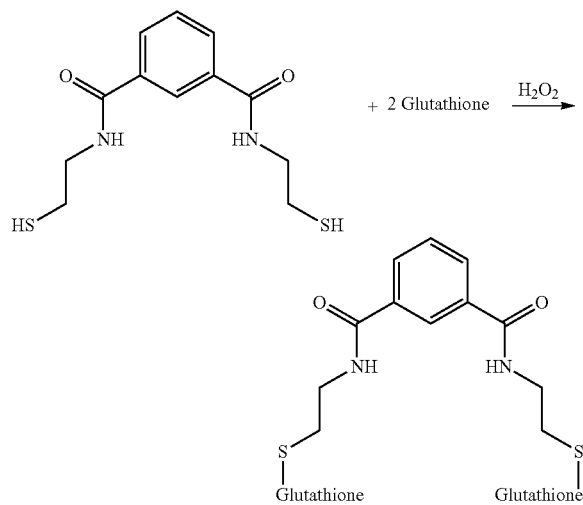

0.284 grams (1 mM) of B9 was dissolved in tetrahydrofuran (THF)/H₂O (50:50 v:v) with 0.76 grams glutathione. 1 mL of 10% H₂O₂ was added with stirring and allowed to react overnight at room temperature. The reaction mix was pumped through a diethylaminoethyl-cellulose (DEAE cellulose) column (2 cm by 20 cm long) in the hydroxide form and washed with 200 ml of distilled water. Bound material was eluted using a 0-400 mM gradient of triethylammonium bicarbonate (TEAB) buffer with 10 mL fractions being collected. Elution of B9 containing product was monitored by an ultraviolet flow-through device. Only one peak was detected in the material that bound to the DEAE cellulose and eluted with the elution buffer. Collected fractions containing UV absorbance were evaporated to dryness over four co-evaporations with methanol/water to remove TEAB. The resulting material was a fine white powder that readily dissolved in water and provided an ultraviolet spectra nearly identical to the starting material (B9). The structure of this compound (termed GB9) is set forth above. The material was tested by thin-layer chromatography (TLC) by two different TLC procedures. On a silica gel matrix developed with 50:50 THF/ethanol, the Rf values for the starting and ending compound were 0.5 and 0.05, respectively. On a PEI-cellulose matrix developed with 0.4 M ammonium bicarbonate solution the Rf values for B9 and GB9 were 0.0 and 0.75, respectively.

In addition, GAB9, GMEAB9 and GEEAB9 may also be synthesized utilizing similar methods.

EXAMPLE 5

2.80 grams of AB9 (7.5 mmol) dissolved in 75 mL of 95% ethanol was added to a stirred solution of 2.0 grams of Cd(C₂H₃O₂)₂.2H₂O (7.5 mmol) dissolved in 100 mL of deionized water. A white precipitate, the compound AB9-Cd, formed upon mixing of the two solutions. The mixture was stirred 7-8 hours before being filtered under vacuum. The resulting white compound was rinsed three times each with 100 mL of deionized water and 100 mL of 95% ethanol. The compound was then dried under vacuum, producing a yield of 2.13 grams. The melting point of the compound was 241-244° C. The compound was insoluble in water, ethanol, acetone, dimethyl sulfoxide, chloroform and hexane.

EXAMPLE 6

0.99 grams of AB9 (2.66 mmol) dissolved in 75 mL of 95% ethanol was added to a stirred solution of 0.71 grams of HgCl₂ (2.61 mmol) dissolved in 100 mL of deionized water. A white precipitate, the compound AB9-Hg, formed upon mixing of the two solutions. The mixture stirred 6 hours before being filtered under vacuum. The white compound was rinsed three times each with 100 mL of deionized water and 100 mL of 95% ethanol. The compound was then dried under vacuum, producing a yield of 0.97 grams. The melting point of the compound was 153-155° C. The compound was insoluble in water, ethanol, acetone, dimethyl sulfoxide, chloroform and hexane.

EXAMPLE 7

2.0 grams of AB9 (5.4 mmol) dissolved in 75 mL of 95% ethanol was added to a stirred solution of 1.5 grams of PbCl₂ (5.4 mmol) dissolved in 150 mL of deionized water. A white precipitate, the compound AB9-Pb, formed upon mixing of the two solutions. The mixture was stirred 7-8 hours before being filtered under vacuum. The white compound was rinsed three times each with 100 mL of deionized water and 100 mL of 95% ethanol. The compound was then dried under vacuum, producing a yield of 1.68 grams. The melting point of the compound was 220-225° C. The compound was insoluble in water, ethanol, acetone, dimethyl sulfoxide, chloroform or hexane.

EXAMPLE 8

192 milligrams of MEAB9 (0.5 mmol) dissolved in 20 mL ethanol was added to a stirred solution of 130 milligrams of HgCl₂ (0.5 mmol) dissolved in 20 mL deionized water. A white precipitate, the compound MEAB9-Hg, formed upon mixing of the two solutions. The mixture stirred for 5 hours before being filtered under vacuum. The white compound was washed with 200 mL of deionized water and 200 mL of ethanol and dried under air to produce a yield of 0.16 grams. The melting point of this compound was 166-169° C. The compound was soluble in dimethyl sulfoxide and highly basic water.

EXAMPLE 9

200 milligrams of EEAB9 (0.5 mmol) dissolved in ethanol was added to a stirred solution of 0.71 grams of HgCl₂ (0.5 mmol) dissolved in deionized water. A white precipitate, the compound EEAB9-Hg, formed upon mixing of the two solutions. The mixture was stirred for 5 hours before being filtered under vacuum. The white compound was washed with 150 mL of deionized water and 150 mL of ethanol and dried under air to produce a yield of 0.20 grams. The melting point of the compound was 150-153° C. The compound was soluble in dimethyl sulfoxide and highly basic water.

EXAMPLE 10

EEAB9 (as detailed in Example 3 above) was injected subcutaneously into rats at levels as high as 1.5 millimoles per kg of body weight. This represented 100 to 1,000 times the concentration expected to be used in chelation therapies for heavy metal toxicity. No detectable negative effects were observed as determined by physical activity and weight gain.

EXAMPLE 11

Rats were injected every three days with the EEAB9 (as detailed in Example 3 above) at 300, 400 and 1,500 micromoles per kg body weight with no observable toxic effects or weight loss. This represented an exposure of over 2,700 micromoles per kg body weight over a 10 day period with no observable toxic effect.

EXAMPLE 12

Individual goldfish were placed in 200 ml water with 10 mM sodium chloride in 250 ml Erlenmeyer flasks (pH 7.00). Air was pumped into the flasks to maintain a healthy supply of oxygen. The 24 hour day was divided in to a 12 hour light/dark photoperiod. The goldfish were allowed to acclimatize for a week before the experiment was conducted, with daily water changes. Goldfish were fed standard fish food for 15 minutes each day before the water was changed.

The chelate ligands were dissolved in dimethyl sulfoxide (DMSO, 0.5 ml) before addition to the flasks. The experimental treatments evaluated are as listed in Table 1 below, and included mercuric acetate, B9, EEAB9, GB9, GEEAB9, and DMSO in the amounts shown in Table 1. B9 and EEAB9 were dissolved in DMSO (0.5 ml) before addition to the water. No precipitate was formed during the dissolution. When mercuric acetate solution in water was added, a precipitate formed, As shown in Table 1, the goldfish exposed to mercuric acetate without chelator died within 30 minutes, whereas the fish exposed to the chelate ligands according to the present disclosure did not die even when exposed to lethal levels of mercuric acetate.

TABLE 1

Exposure of goldfish to mercuric acetate with and without chelators.

| Flask | Compound | Amount | 30 min | 1 hr | 6 hr | 12 hr | 24 hr |
|---|---|---|---|---|---|---|---|
| 1 | Mercuric acetate | 0.5 mM | Dead | | | | |
| 2 | Mercuric acetate | 0.5 mM | Dead | | | | |
| 3 | CT01 | 1.0 mM | Alive | Alive | Alive | Alive | Alive |
| 4 | CT01 | 1.0 mM | Alive | Alive | Alive | Alive | Alive |
| 5 | CT03 | 1.0 mM | Alive | Alive | Alive | Alive | Alive |
| 6 | CT03 | 1.0 mM | Alive | Alive | Alive | Alive | Alive |
| 7 | CT01 + Mercuric acetate | 1.0 mM + 0.5 mM | Alive | Alive | Alive | Alive | Alive |
| 8 | CT01 + Mercuric acetate | 1.0 mM + 0.5 mM | Alive | Alive | Alive | Alive | Alive |
| 9 | CT03 + Mercuric acetate | 1.0 mM + 0.5 mM | Alive | Alive | Alive | Alive | Alive |
| 10 | CT03 + Mercuric acetate | 1.0 mM + 0.5 mM | Alive | Alive | Alive | Alive | Alive |
| 11 | CT01G | 1.0 mM | Alive | Alive | Alive | Alive | Alive |
| 12 | CT01G | 1.0 mM | Alive | Alive | Alive | Alive | Alive |
| 13 | CT01G + Mercuric acetate | 1.0 mM + 0.5 mM | Alive | Alive | Alive | Alive | Alive |
| 14 | CT01G + Mercuric acetate | 1.0 mM + 0.5 mM | Alive | Alive | Alive | Alive | Alive |
| 15 | CT03G + Mercuric acetate | 1.0 mM + 0.5 mM | Alive | Alive | Alive | Alive | Alive |
| 16 | CT03G + Mercuric acetate | 1.0 mM + 0.5 mM | Alive | Alive | Alive | Alive | Alive |
| 17 | Mercuric acetate + DMSO | 0.5 mM + 0.5 ml | Dead | | | | |
| 18 | Mercuric acetate + DMSO | 0.5 mM + 0.5 ml | Dead | | | | |
| 19 | CONTROL (DMSO) | 0.5 ml | Alive | Alive | Alive | Alive | Alive |
| 20 | CONTROL (DMSO) | 0.5 ml | Alive | Alive | Alive | Alive | Alive |
| 21 | CONTROL | | Alive | Alive | Alive | Alive | Alive |
| 22 | CONTROL | | Alive | Alive | Alive | Alive | Alive |

EXAMPLE 13

In this example, AB9 loaded polystyrene (PS-AB9) was attempted by first derivatizing PS-CH$_2$Cl. This follows the literature procedure found in Roscoe, S. B., et. al, *Journal of Polymer Science: Part A: Polymer Chemistry,* 2000, 38, 2979-2992. First PS-CH$_2$-NHEt was prepared.

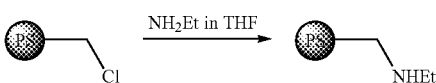

PS beads were stirred with 2.0 M solution of ethylamine in THF for 2 days and then rinsed with water and THF and a series of (v/v) mixtures of water/THF (2:1, 1:1, 1:2) to purify the product which was then dried at about 40° C. The product was characterized by infrared spectroscopy and found to match the spectrum found in the literature.

Second, the acid group of AB9 was bound to the amine group of PS-CH$_2$-NHEt.

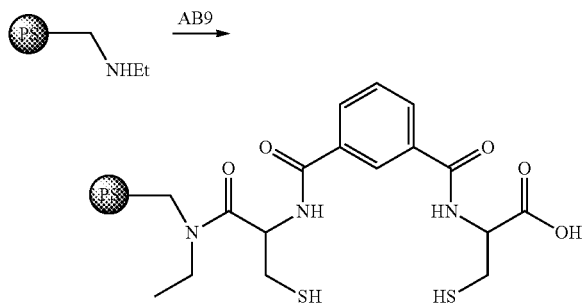

PS-CH$_2$-NHEt was stirred with an ethanol or methanol solution of AB9 for about 24 hours. In the alternative, other solvents such as pyridine could also be used. The beads were washed with ethanol or methanol and dried at about 40° C. The product was characterized by infrared spectroscopy and elemental analysis.

EXAMPLE 14

In this example PS-AB9 was prepared by derivatizing polystyrene beads but on a 20 g scale. Polystyrene beads (20 g) were stirred with 120 ml 2.0 M solution of ethylamine in THF for 2 days. After 2 days, the beads were then filtered and rinsed with 200 mL of THF and 200 mL of water and a series of (v/v) mixtures of water/THF (2:1, 1:1, 1:2, 200 mL each) and then dried at about 40° C. PS-CH$_2$-NHEt beads (20 g) where then refluxed with AB9 (30 g) in 300 mL of ethanol for about two days. The beads were filtered and washed about five times with 200 mL of ethanol and dried at about 40° C. The products from each step were characterized by infrared spectroscopy.

EXAMPLE 15

In this characterization, the loading of AB9 on derivatized polystyrene (5 and 20 g scales) was determined. PS-CH$_2$-AB9 beads (500 mg) were digested at 110° C. by the addition of 10 mL of water, 10 mL concentrated HNO$_3$, 10 mL 1:1 HNO$_3$, 5 mL H$_2$O$_2$ and 10 mL concentrated HCl. After digestion, the solutions were filtered to isolate the beads and the final volume of sample was 50 mL. The solutions were then analyzed by ICP to determine the sulfur content which indicates the amount of AB9 bound on the polystyrene.

| Sulfur Loading on PS-AB9 (5 g Scale) | | | | | | | | | |
|---|---|---|---|---|---|---|---|---|---|
| g S/0.5 g beads | mmol S/0.5 g beads | mmol AB9/ 0.5 g beads | mmol AB9/g of PS-AB9 | g of AB9/g of PSAB 9 | mmol of Cl/ g of PS-AB9 | low % AB9 loading | high % AB9 loading | Removal of g Hg/g of PSAB9 (Theo.) | Removal of mmol Hg/g of PSAB9 (Theo.) |
| 0.007 | 0.22 | 0.11 | 0.22 | 0.08 | 1.0-1.5 | 15 | 22 | 0.044 | 0.22 |

| Sulfur Loading on PS-AB9 (20 g Scale) | | |
|---|---|---|
| Sample | mg/L S (in solution) | g S/kg PS (loading) |
| 1 | 13.93 ± 0.45 | 1.39 ± 0.04 |
| 2 | 14.17 ± 0.20 | 1.42 ± 0.02 |
| 3 | 14.03 ± 0.04 | 1.40 ± 0.00 |
| average | 14.04 ± 0.23 | 1.40 ± 0.02 |

EXAMPLE 16

In this example Hg binding with PS-AB9 was tested. PS-CH$_2$-AB9 (202 mg, 400 mg and 600 mg) was added to HgCl$_2$ (15 ppm) in 25 ml of water and stirred one day at room temperature. After stirring, the beads were isolated by filtering through a 0.2 μm environmental express filter and the solutions were digested for inductively coupled plasma spectrometry analysis. This was conducted at 110° C. by sequentially adding, 10 mL 1:1 HNO$_3$, 5 mL conc. HNO$_3$, 5 mL H$_2$O$_2$ and 10 mL conc, HCl.

| Hg Binding by PS-AB9 | | |
|---|---|---|
| Solution | Calc Conc. (ppm) | % Hg Bound |
| Stock solution | 3.874 ± 0.073 | N/A |
| 0.2 gm PSAB9 | 1.963 ± 0.029 | 49.3% |
| 0.4 gm PSAB9 | 0.826 ± 0.015 | 78.7% |
| 0.6 gm PSAB9 | 0.798 ± 0.016 | 79.4% |

EXAMPLE 17

In this example, AB9 loaded polystyrene was attempted using a direct reaction. While this procedure has yet to be successfully demonstrated, it is likely that the reaction can be made successful by changing reagents, conditions and other variables.

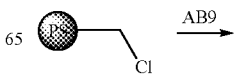

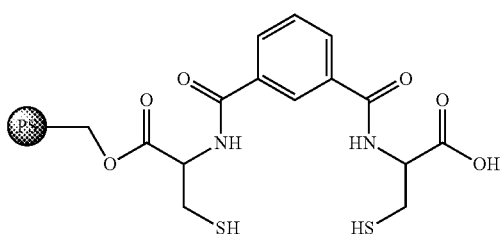

A solution of excess AB9 in ethanol could be added to polystyrene beads (chloromethylated polystyrene-co-divinylbenzene (2% DVB) (200-400 mesh). This may ensure that each polystyrene bead reacted with an excess of AB9 to prevent cross-linking of the ligand. The mixture could be stirred for ~24 hours with and without heating to drive off HCl. If the resulting solution is acidic, any remaining acid could be neutralized with 5% NaHCO$_3$. Alternatively, NEt$_3$ may be added with the ligand solution, without heating, to effect HCl elimination as [HNEt$_3$]Cl. The beads may then be washed with ethanol and water and dried at ~40° C. Infrared characterization could be conducted to observe the PS-attached group, SH, NH and the remaining carboxylate. Elemental analysis could be used to determine the amount of AB9 present on the PS beads. Additionally, the PS-AB9 may be treated with dilute HCl and the AB9 isolated and analyzed.

EXAMPLE 18

In this example, amine-functionalized silica (SiNH$_2$) was produced for AB9 binding. This was conducted following the procedure set forth in: Cai, M. et al, *Journal of Molecular Catalysis A: Chemical.* 2007, 268, 82 and Jyothi, T. M., et al; *Chem. Int. Ed.* 2001, 40, 2881. A suspension of silica-60 (20 g) in toluene (500 mL) was refluxed with γ-aminopropyltriethoxysilane (15.70 g, 71.36 mmol) in chloroform (40 mL) at ~100° C. for 48 h. After refluxing, the solid was filtered and washed with CHCl$_3$ (5×80 mL), and dried under vacuum for 12 h. The dried solid was then soaked in a solution of Me$_3$SiCl (31.28 g, 286.97 mmol) in toluene (350 ml) at room temperature for 24 h. After soaking, the solid was filtered and washed with acetone (10×40 mL) and diethyl ether (10×15 mL) and dried under vacuum at 100° C. for 5 h. This resulted in isolation of 25.81 g of solid. Me$_3$SiCl will bind with any unreacted —OH on the solid to form —OSiMe$_3$ to block the reactivity of the hydroxyl groups on the silica surface.

Derivatization of Silica Surface with
γ-Aminopropyltriethoxysilane

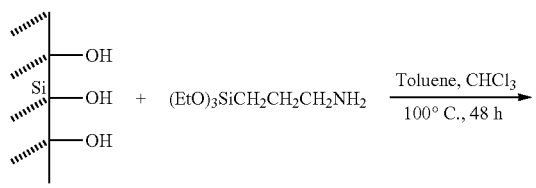

SiMe$_3$Cl Derivatization of Unprotected Hydroxyl Groups

From literature, the inclusion of thiol functionalities on the surface of silica particles is characterized by elemental analysis (Cai, 2007), powder X-ray diffraction and scanning electron microscopy (Nakamura, 2007). Elemental analysis provides nitrogen content on the silica particle. X-ray diffraction is used to find out the regularity of particles and the change in particle size was determined by scanning electron microscopy.

Infrared Spectroscopy (cm$^{-1}$) was used to determine the functionality (—NH$_2$, —CH$_2$—, —OH) on the silica surface. A broad peak at 3434 and 3050 (—CH$_2$—) was observed. It was found that the peak intensity at 3459 was decreased drastically after treatment of silica particles with amine. Elemental analysis of Si—NH$_2$ (%) produced: C 7.71; H 2.42; N 2.72; O 9.37; Si 32.87; S 0.03; (Silica-60: C 0.05; H 1.26; N 0.01; O 7.22; Si 42.60; S<0.01). The nitrogen content was found to be 1.94 mmol/g SiNH$_2$/g Si60.

Figure 2:
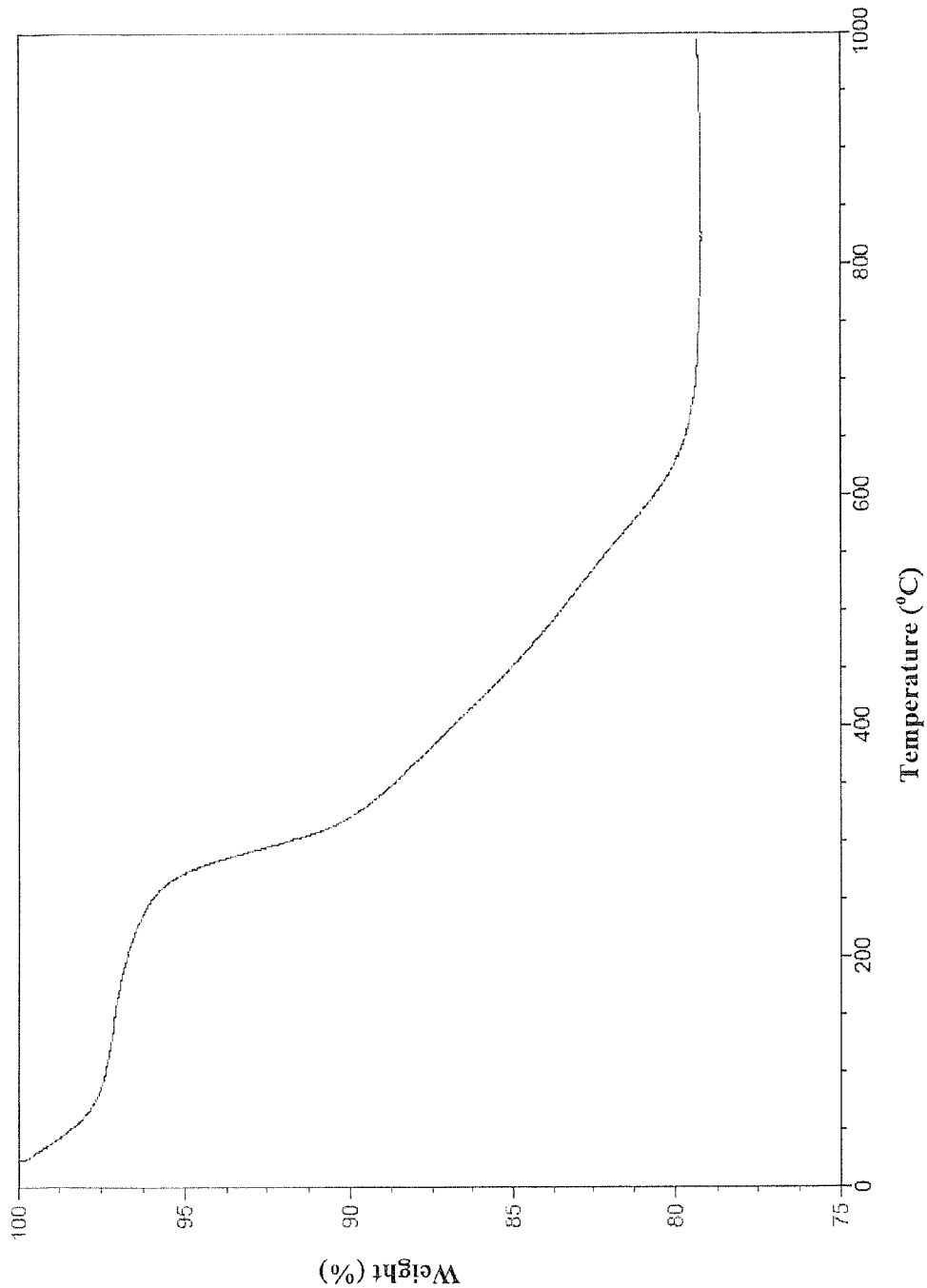
FIG. 2 shows the weight loss results of a thermogravimeteric analysis on $SiNH_2$ from a temperature range of 30° C. to 1000° C. with a temperature increase of 20° C./min and a flow rate of 110/55 mmHg (inlet/outlet pressure) performed at air atmosphere.

Referring now to FIG. 1 and FIG. 2, thermogravimetric analysis was performed on Silica-60 and SiNH$_2$ at a temperature range of 30° C. to 1000° C., a temperature increase of 20° C./min; and a flow rate of 110/55 mmHg (inlet/outlet pressure); all at air atmosphere. The TGA analysis of Silica-60 (Si60), SiNH$_2$ showed that the pattern of weight loss changed significantly when Si60 was treated with γ-aminopropyltriethoxysilane. The initial weight losses in both traces correspond to loss of coordinated water. The Si60 with terminal hydroxyl groups is capable of hydrogen bonding a much larger amount of water than the Si60-NH$_2$. Subsequent heating of Si60 causes condensation of the terminal hydroxyl groups to eliminate water. For Silica-60-NH$_2$ the mass loss represents loss of the organic amine from the silica surface.

EXAMPLE 19

In this example the binding of AB9 on a silica surface modified with amine (SiNH$_2$) was performed wherein two different methods were attempted to functionalize the silica surface.

Under the first method, SiNH$_2$ (9.0 g) solid in N,N'-dimethyl formamide (DMF) (200 mL) was stirred with AB9 (6.5 g, 17.43 mmol) in the presence of dicyclohexylcarbodiimide (DCC, 14.63 mmol, 3.0 g) and diisopropylethylamine (DIPEA, 22.82 mmol, 4 mL) for 6 h. The solid was then filtered and washed with DMF (200 mL), dichloromethane (DCM, 250 mL) and methanol (250 mL). After washing, the solid was dried under vacuum for 8 h. This resulted in isolation of 8.41 g of solid.

From literature, the inclusion of thiol functionalities on the surface of silica particles is characterized by elemental analysis (Cai, 2007), Raman spectroscopy, powder X-ray diffraction and scanning electron microscopy (Nakamura, 2007). Due to strong Raman scattering, the thiol groups are detected by Raman spectroscopy. Elemental analysis provides nitrogen content on the silica particle. X-ray diffraction is used to find out the regularity of particles and the change in particle size was determined by scanning electron microscopy.

Infrared spectroscopy (cm$^{-1}$) produced a broad peak at 3440 and very small peak at 3050. Also there was peak at 1538 (—NH). Elemental Analysis (%) produced: C 8.34; H 2.42; N 2.75; O 6.85; Si 34.05; S 0.22; (Si60: C 0.05; H 1.26; N 0.01; O 7.22; Si 42.60; S<0.01). The sulfur content was also found to be 0.034 mmol SiAB9/g of Si60.

Figure 3:
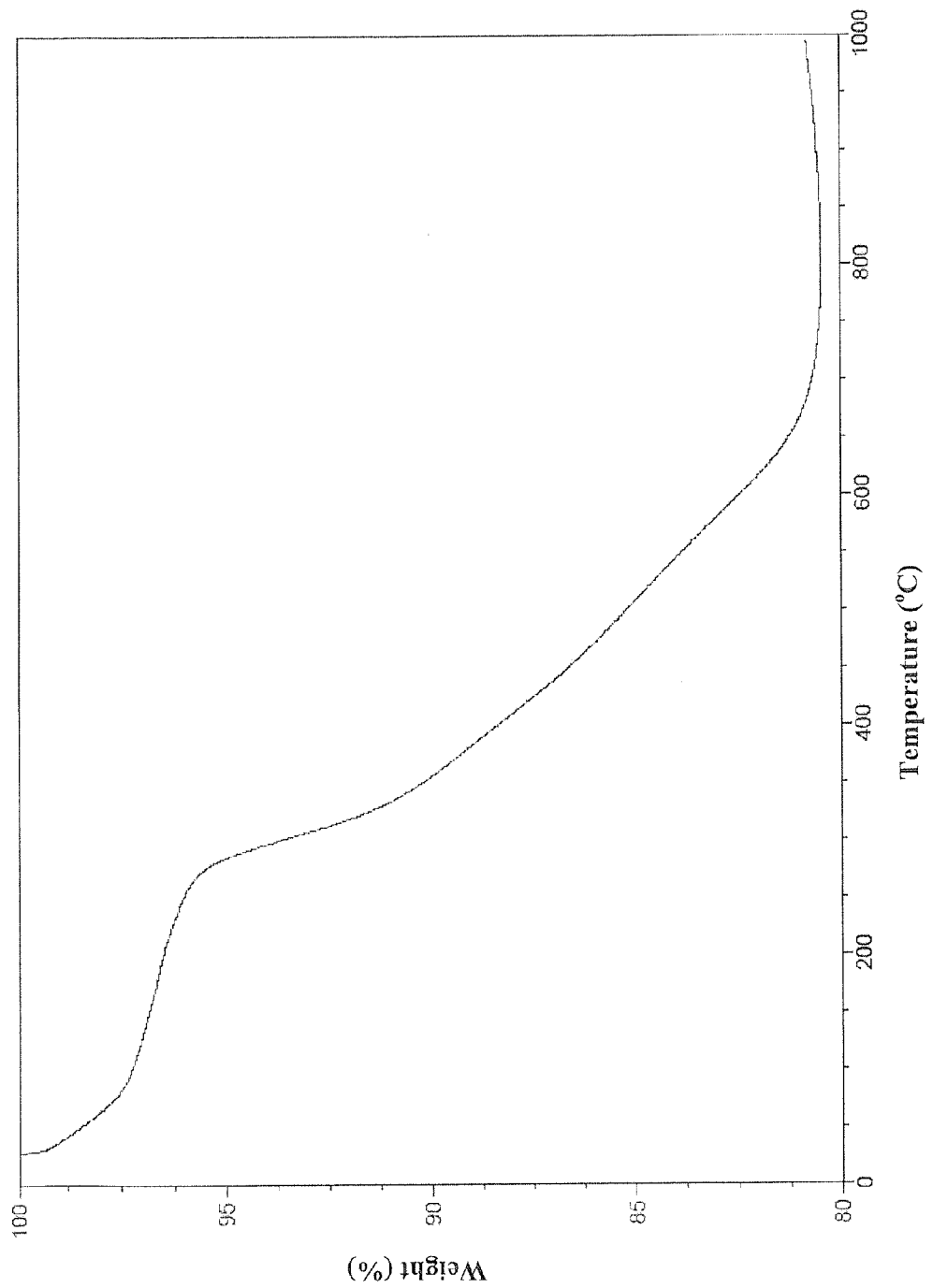
FIG. 3 shows the weight loss results of a thermogravimeteric analysis on SiAB9 produced from a first experimental procedure from a temperature range of 30° C. to 1000° C. with a temperature increase of 20° C./min and a flow rate of 110/55 mmHg (inlet/outlet pressure) performed at air atmosphere.

Referring now to FIG. 3, thermogravimetric analysis was performed on SiNH$_2$ treated with AB9 in the presence of DCC at a temperature range of −30° C. to 1000° C., a temperature increase of 20° C./min; and a flow rate of 110/55 mmHg; all at air atmosphere. It was found that there is no significant change in thermogravimetric analysis of SiAB9. This might be due to small amount of AB9 present per g of SiAB9. But the pattern of TGA of SiAB9 synthesized by refluxing in EtOH changed from the TGA of SiNH$_2$. This might be due to larger amount of AB9 per g of SiAB9, which is also evident from the ICP analysis data of sulfur.

Inductively coupled plasma spectrometry was further performed. SiAB9 beads (500 mg) were digested at 110° C. by addition of 10 mL water, 10 mL 1:1 HNO$_3$, 5 mL conc. HNO$_3$, 5 mL H$_2$O$_2$ and 10 mL conc. HCl. After digestion, the solutions were filtered to isolate the beads and the final volume of the sample was 50 mL. The solutions were then analyzed by ICP to determine the sulfur content:

| Sulfur loading on SiAB9-10 g scale | | | | | |
|---|---|---|---|---|---|
| g S/0.5 g beads | mmol S/0.5 g beads | mmol AB9/g of SiAB9 | g of AB9/g of SiAB9 | Removal of mmols Hg/g of SiAB9 (Theo.) | Removal of g Hg/g of SiAB9 (Theo.) |
| 0.0013 | 0.04 | 0.04 | 0.015 | 0.04 | 0.008 |

| Sulfur loading on SiAB9-10 g scale | | |
|---|---|---|
| Sample | mg/L S (in solution) | g S/kg SiAB9 (loading) |
| 1 | 2.57 ± 0.04 | 0.13 ± 0.00 |
| 2 | 2.75 ± 0.12 | 0.14 ± 0.00 |
| average | 2.66 ± 0.08 | 0.135 ± 0.00 |

Under the second method, SiNH$_2$ (9.0 g) was refluxed in a solution of AB9 (22.78 mmol, 8.50 g) in ethanol (500 mL) for 24 h. After refluxing, the solid was filtered and washed with ethanol (12×50 mL) and dried under vacuum. This resulted in isolation of 8.6 g of solid.

Reaction of SiNH$_2$ and AB9 with Heating

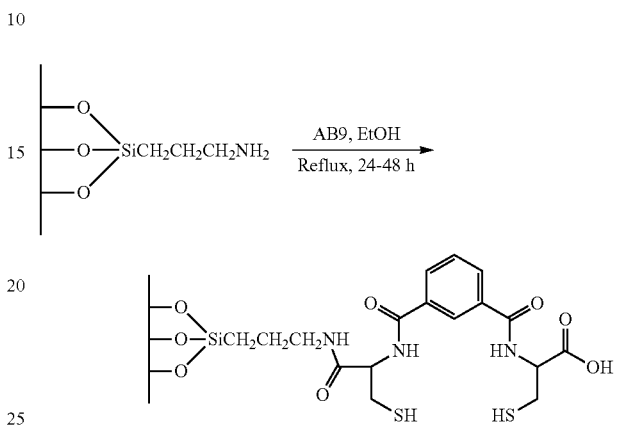

Characterization was performed following the methods used for the first method. Infrared spectroscopy (cm$^{-1}$) produced a broad peak at 3440 and also broad and very small peak at 3050. There was another peak at 1515 (—NH). Elemental analysis (%) produced: C 10.33; H 2.68; N 2.89; O 12.04; Si 26.88; S 0.76; (Si60: C 0.05; H 1.26; N 0.01; O 7.22; Si 42.60; S<0.01). The sulfur content was also found to be 0.24 mmol/g of SiAB9. The EA data showed that the second experimental method (refluxing in EtOH) gave the higher AB9 loading than the first experimental method (using DCC and other reagents). SiAB9 obtained from refluxing EtOH had 0.12 mmol of AB9/g of beads (0.24 mmol of S/g of beads) which is in good agreement with the value obtained from the sulfur analysis by inductively coupled plasma spectroscopy.

Figure 4:
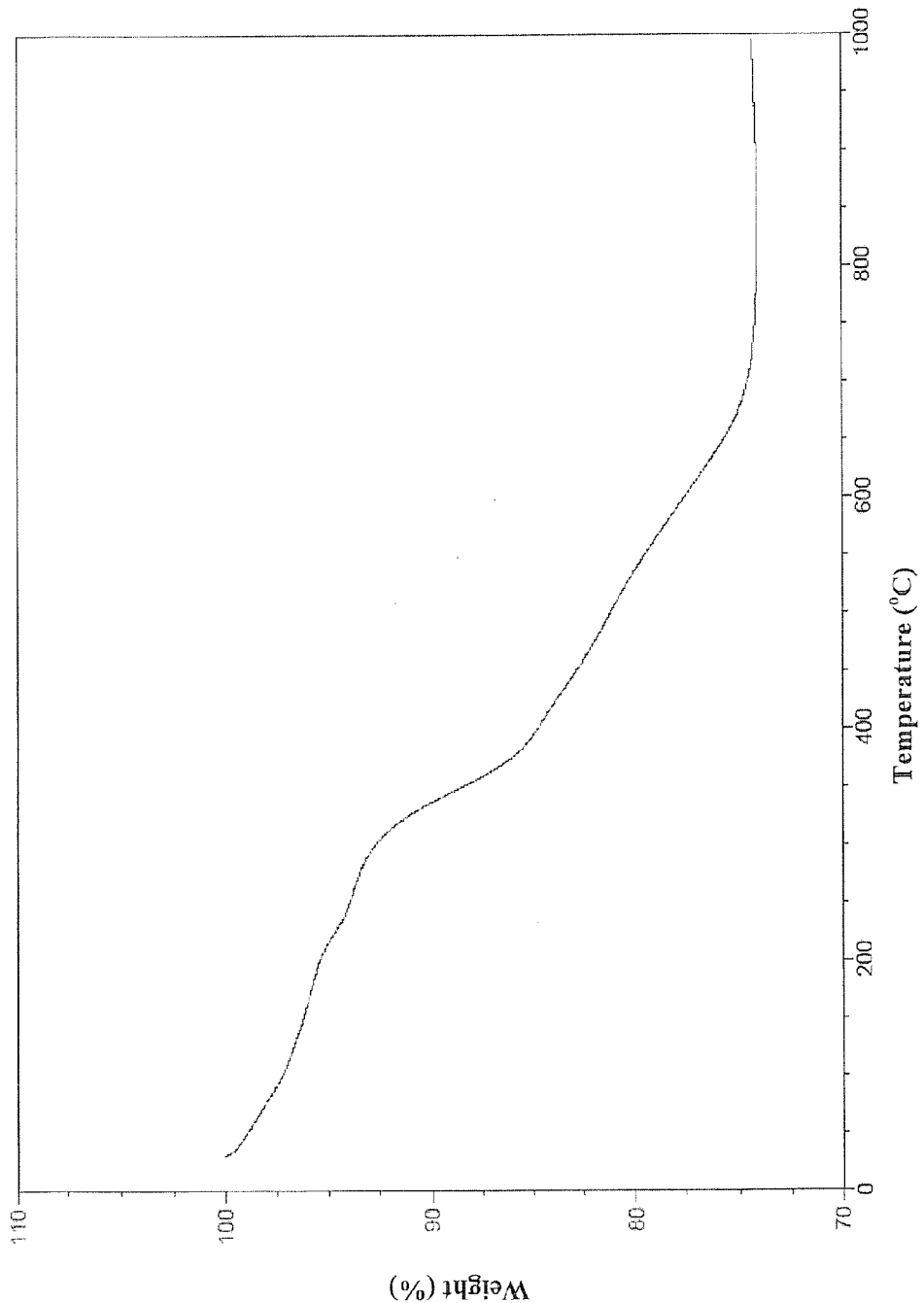
FIG. 4 shows the weight loss results of a thermogravimeteric analysis on SiAB9 produced from a second experimental procedure from a temperature range of 30° C. to 1000° C. with a temperature increase of 20° C./min and a flow rate of 110/55 mmHg (inlet/outlet pressure) performed at air atmosphere.
Figure 5:
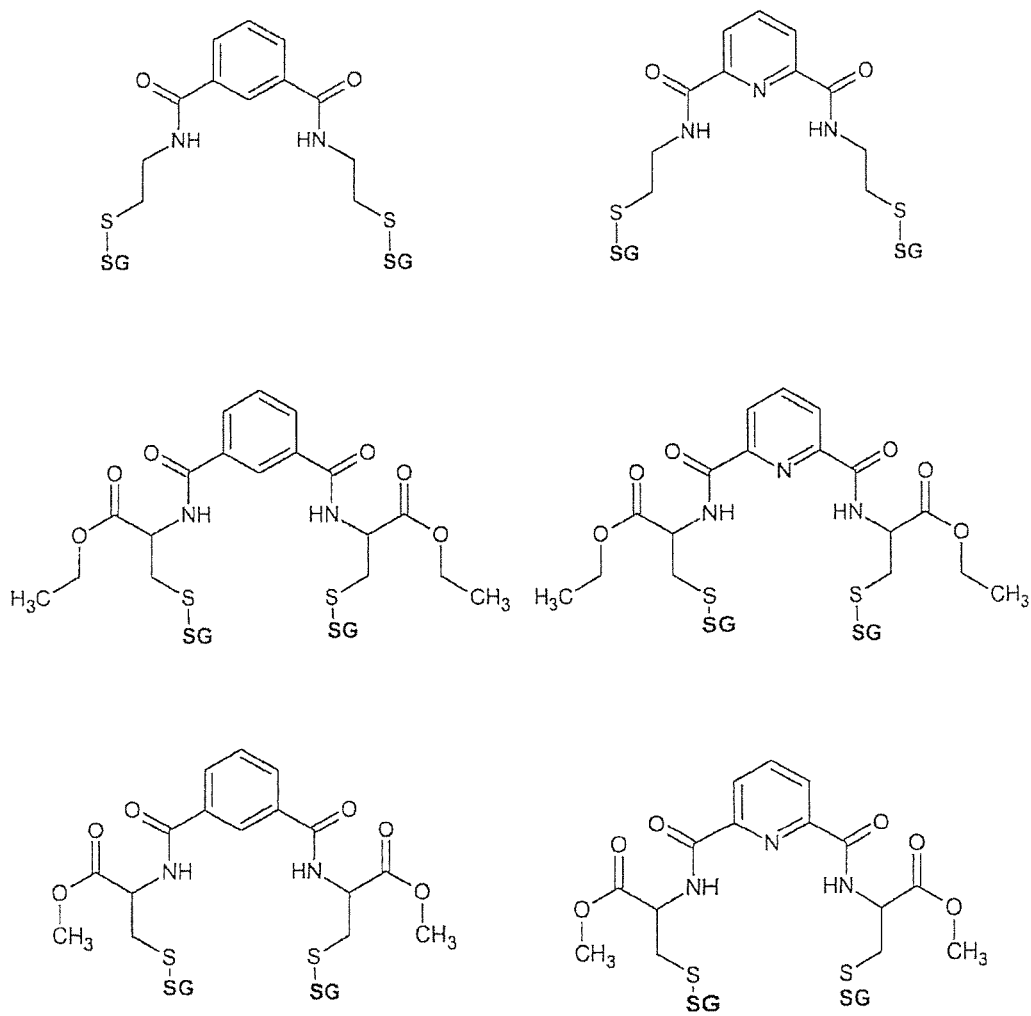
FIG. 5 shows the chemical structures of various hydrophobic chelators according to the present invention, which are converted to hydrophilic chelators within the microenvironment.
Figure 6A:
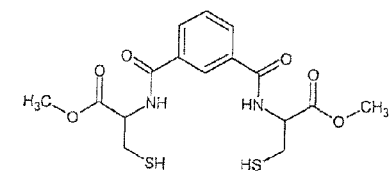
FIGS. 6a and 6b show the chemical structures of various chelators according to the present invention, which may be introduced into a body in a hydrophilic state, reduced to a hydrophobic state in the body for partitioning into lipid-rich areas, and subsequently enzymatically returned to a hydrophilic state iii vivo.
Figure 6A:
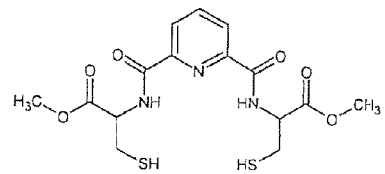
Figure 6A:
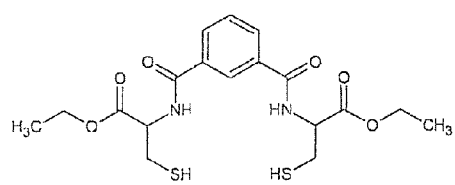
Figure 6A:
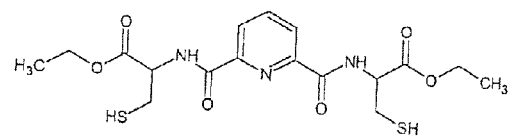
Figure 6A:
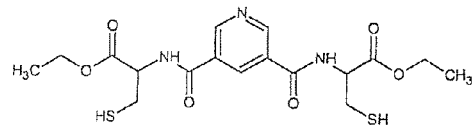
Figure 6A:
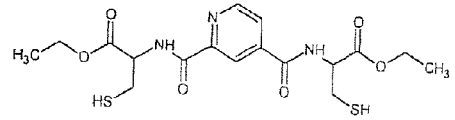
Figure 6A:
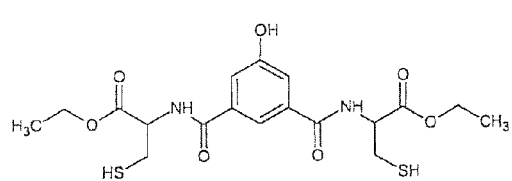
Figure 6A:
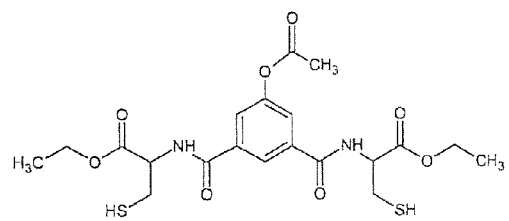
Figure 6B:
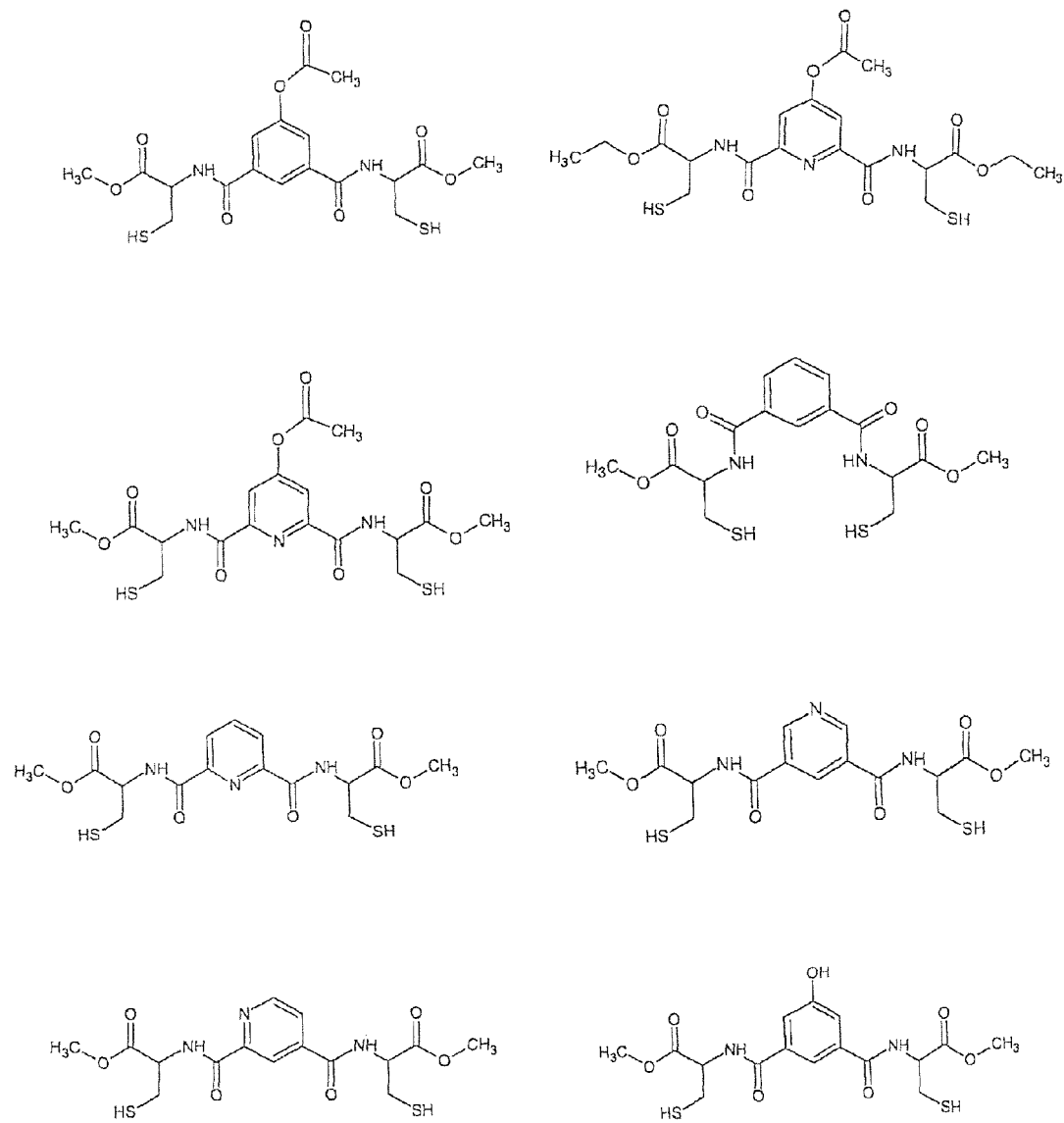

Referring now to FIG. 4, thermogravimetric analysis was performed on SiNH$_2$ treated with AB9 refluxed in EtOH at a temperature range of 30° C. to 1000° C., a temperature increase of 20° C./min; and a flow rate of 110/55 mmHg; all at air atmosphere. Furthermore, inductively coupled plasma analysis was performed. SiAB9 beads (500 mg) were digested at 110° C. by addition of 10 mL water, 10 mL 1:1 HNO$_3$, 5 mL conc. HNO$_3$, 5 mL H$_2$O$_2$ and 10 mL conc. HCl. After digestion, the solutions were filtered to isolate the beads and the final volume of sample was 50 mL. The solutions were then analyzed by ICP to determine the sulfur content:

| Sulfur loading on SiAB9-10 g prep | | | | | |
|---|---|---|---|---|---|
| g S/0.5 g beads | mmol S/0.5 g beads | mmol AB9/g of SiAB9 | g of AB9/g of SiAB9 | Theoretical mmol Hg/g of SiAB9 | Theoretical g Hg/g of SiAB9 (Theo.) |
| 0.004 | 0.14 | 0.14 | 0.05 | 0.14 | 0.027 |

| Sulfur loading on SiAB9-10 g prep | | |
| --- | --- | --- |
| Sample | mg/L S (in solution) | g S/kg SiAB9 (loading) |
| 1 | 8.62 ± 0.02 | 0.43 ± 0.00 |
| 2 | 8.71 ± 0.20 | 0.44 ± 0.02 |
| average | 8.67 ± 0.11 | 0.435 ± 0.01 |

As the specific surface BET of Si60 is 500 m²/g, the AB9 coverage is 0.14 mmol/500 m²/g.

EXAMPLE 20

In this example aqueous Hg(II) was remediated with a combination of Si60 and SiAB9 with $HgCl_2$. It was found that loading of AB9 per g of SiAB9 is higher in the SiAB9 obtained from the second experimental method. Therefore, the Hg remediation in the solution phase was conducted using SiAB9 obtained from refluxing EtOH.

Si60 (200 mg and 600 mg) was added to $HgCl_2$ (~5 ppm) in water (50 mL) and stirred for 1 day at room temperature. The pH of the solution was 5.5-6.0 and was monitored by Corning 313 pH meter. After stirring, the beads were isolated by filtration through a 0.2 μm filter (Environmental Express) and the solutions were digested for ICP analysis. This was conducted at 110° C. by adding, 10 mL 1:1 $HNO_3$, 5 mL conc. $HNO_3$, 5 mL $H_2O_2$ and 10 mL conc. HCl. The removal of Hg by Si60 was then determined:

| Determination of Hg removal by Si60 | | |
| --- | --- | --- |
| Solution | Calc Conc. (ppm) | % Removal |
| Stock solution | 5.823 ± 0.071 | N/A |
| 0.2 g Si60 | 4.425 ± 0.047 | 24% |
| 0.6 g Si60 | 2.895 ± 0.058 | 50% |

SiAB9 (200 mg and 600 mg) was added to $HgCl_2$ (~5 ppm) in water (50 mL) and stirred for 1 day at room temperature. pH of the solution was 5.5-6.0 and was monitored by Corning 313 pH meter. After stirring, the beads were isolated by filtration through a 0.2 μm filter (Environmental Express) and the solutions were digested for ICP analysis. This was conducted at 110° C. by sequentially adding, 10 L 1:1 $HNO_3$, 5 mL conc. $HNO_3$, 5 mL $H_2O_2$ and 10 mL conc. HCl.

The removal of Hg by SiAB9 was then determined:

| Determination of Hg Removal by SiAB9 | | |
| --- | --- | --- |
| Solution | Calc Conc. (ppm) | % Removal |
| Stock solution | 5.823 ± 0.071 | N/A |
| 0.2 g SiAB9 | 0.316 ± 0.002 | 95% |
| 0.6 g SiAB9 | 0.173 ± 0.024 | 97% |

The Hg remediation study showed that SiAB9 remediates about 95-97% of Hg with increasing SiAB9 loading. But at the same time it was found that Si60 also remediates 25-50% Hg with increasing Si60 loading. This is probably due to adsorption of Hg on the surface of Silica-60.

EXAMPLE 21

In this example aqueous As(III) was remediated with a combination of Si60 and SiAB9 synthesized by refluxing in EtOH with $NaAsO_2$.

Si60 (200 mg and 600 mg) was added to $NaAsO_2$ (~200 ppb) in water (50 mL) and stirred for 1 day at room temperature. After stirring, the beads were isolated by filtration through a 0.45 μm filter (Environmental Express) and the solutions were digested for inductively coupled plasma spectrometry analysis. This was conducted at 95° C. by adding 2.5 mL conc. $HNO_3$.

The removal of As(III) by SiAB9 was then determined at pH levels 5, 7 and 9:

| Determination of As removal by Si60 at pH 5 | | | |
| --- | --- | --- | --- |
| Sample ID | Conc. (μg/L) | Stdev. | % Remed. |
| As stock | 208.45 | ±10.86 | N/A |
| 0.2 g Si60 | 207.10 | ±5.59 | 0.6% |
| 0.6 g Si60 | 199.10 | ±3.58 | 4.5% |

| Determination of As removal by Si60 at pH 7 | | | |
| --- | --- | --- | --- |
| Sample ID | Conc. (μg/L) | Stdev. | % Remed. |
| As stock | 225.80 | ±0.23 | N/A |
| 0.2 g Si60 | 214.50 | ±5.36 | 5.0% |
| 0.6 g Si60 | 203.90 | ±7.75 | 9.7% |

| Determination of As removal by Si60 at pH 9 | | | |
| --- | --- | --- | --- |
| Sample ID | Conc. (μg/L) | Stdev. | % Remed. |
| As stock | 218.20 | ±5.02 | N/A |
| 0.2 g Si60 | 213.90 | ±5.35 | 2.0% |
| 0.6 g Si60 | 206.30 | ±4.74 | 5.5% |

In the SiAB9 (synthesized by refluxing in EtOH) with $NaAsO_2$ remediation of As(III), SiAB9 (200 mg, and 600 mg) was added to $NaAsO_2$ (~200 ppb) in water (50 mL) and stirred for 1 day at room temperature. After stirring, the beads were isolated by filtration through a 0.45 μm filter (Environmental Express) and the solutions were digested for inductively coupled plasma spectrometry analysis. This was conducted at 95° C. by adding 2.5 mL conc. $HNO_3$.

The removal of As(III) by SiAB9 was then determined at pH levels 5, 7 and 9:

| Determination of As removal by SiAB9 at pH 5 | | | |
| --- | --- | --- | --- |
| Sample ID | Conc. (μg/L) | Stdev. | % Remed. |
| As stock | 208.45 | ±10.86 | N/A |
| 0.2 g Si AB9 | 115.40 | ±7.27 | 44.6% |
| 0.6 g Si AB9 | <5.0 | N/A | 100% |

Determination of As removal by SiAB9 at pH 7

| Sample ID | Conc. (μg/L) | Stdev. | % Remed. |
|---|---|---|---|
| As stock | 225.80 | ±0.23 | N/A |
| 0.2 g Si AB9 | 137.00 | ±1.78 | 39.3% |
| 0.6 g Si AB9 | 64.30 | ±2.96 | 71.5% |

Determination of As removal by SiAB9 at pH 9

| Sample ID | Conc. (μg/L) | Stdev. | % Remed. |
|---|---|---|---|
| As stock | 218.20 | ±5.02 | N/A |
| 0.2 g SiAB9 | 156.80 | ±10.98 | 28.1% |
| 0.6 g Si AB9 | <5.0 | N/A | 100.0% |

It was found that Si60 alone did not remediate As from aqueous medium. Whereas the efficiency of SiAB9 to remove As decreases with increasing pH at low loading of SiAB9. But with increasing loading, SiAB9 remediates As(III) very efficiently.

EXAMPLE 22

In this example gas phase binding of Hg(0) with Si60 and SiAB9 was explored. Si60-AB9 (from EtOH reaction) with a 0.14 mmol AB9/g loading was used. In the alternative, binding could take place in other fluids (i.e. gasses or liquids) with the presence of the polymer or solid supported chemical compound. In the present example, the sample (3 g) was placed in the filter frit above the permeation tube with the Hg(0) gas flowing at 100 mL/min for one hour through the sample and then passed, with gas dispersion tubes, into two liquid traps containing a 150 mL solution of 5% nitric acid and 10% hydrochloric acid. This captures the Hg(0) that was not caught by the solid sample. The solid sample was taken from the filter fit and washed with ethanol to release any physisorbed Hg(0). Then 2 g of the solid sample was digested using the EPA 30-50B method and analyzed on the ICP along with the traps, which did not need to be digested.

The Silica-AB9 was able to fill 85% of its binding sites with Hg. There were some Hg(0) vapor to pass. However, doing a smaller PTFF run or a larger sample size for an hour may reach the desired 100% Hg(0) vapor capture.

Pharmaceutical compositions according to the present disclosure as set forth above may be prepared by combining a pharmaceutically effective amount of the compounds with a pharmaceutically suitable excipient. Substantially any suitable excipient may be utilized including but not limited to albumin, almond oil, ascorbic acid, benzoic acid, calcium stearate, canola oil, calcium carboxymethylcellulose, sodium carboxymethylcellulose, castor oil, hydrogenated castor oil, microcrystalline cellulose, corn oil, cotton seed oil, cyclodextrins, ethylene glycol palmitostearate, gelatin, glycerin, hydroxyethyl cellulose, hydroxyethylmethyl cellulose, hydroxypropyl cellulose, low-substituted hydroxypropyl cellulose, lanolin, linoleic acid, magnesium silicate, magnesium stearate, medium-chain triglycerides, mineral oil, olive oil, peanut oil, pectin, compressible sugar, sunflower oil, hydrogenated vegetable oil and water. In order to provide multiple antioxidant potential, the pharmaceutical compositions may further include other antioxidants including, but not limited to vitamin-E, vitamin-D, cystine, glutathione, lipoic acid and combinations thereof. Further the pharmaceutical compositions may include a water soluble metal chelator to enhance removal of toxic metals both through the liver and kidney and with an enhanced rate. Substantially, any suitable water soluble metal chelator may be utilized including but not limited to glutathione (GSH), dihydrolipoic acid (DLPA), lipoic acid (LPA), N-acetylcysteine (NAC), dimercaptopropane sulfonate (DMPS), dimercaptosuccinic acid (DMSA), ethylenediaminetetraacetic acid (EDTA), and mixtures thereof. Further, in order to further enhance the levels of glutathione in the subject, the pharmaceutical compositions may include a precursor of glutathione which may be selected from a group including but not limited to cysteine, glycine, glutamate and combinations thereof. Further pharmaceutical compositions may include a dietary supplement that supports glutathione synthesis. Substantially any appropriate dietary supplement that supports glutathione synthesis may be utilized including but not limited to whey protein, N-acetylcystein, cysteine, glutathione, nicotine adenine dinucleotide ($NAD^+$), reduced nicotine adenine dinucleotide (NADH), glycylcysteine (gly-cys), glutamylcysteine (glu-cyc), and combinations thereof.

Pharmaceutical compositions may also include various binders, preservatives, mineral supplements, bulking agents, diluents, carriers, flavoring agents that are widely known to be used in pharmaceutical compositions. Exemplary pharmaceutical compositions include between about 95.5 and about 85 weight percent active compound, between about 0.5 and about 15 weight percent excipient. The optional additional antioxidant(s) may be provided at between about 0 and about 50 weight percent. The optional additional water soluble metal chelator may be provided at between about 0 and about 20 weight percent. The optional additional precursor of glutathione may be provided at between about 0 and about 50 weight percent. Further the optionally additional dietary supplement that supports glutathione synthesis may be provided at between about 0 and about 50 weight percent. One or more of any of the optional additives may be included. The optional additive replaces a like percentage of the compound in the final composition.

Preferred dosage forms for oral administration include the isolated compounds in powder form. Such powders may be taken up with a scoop and spread onto food or mixed into drinks for easy consumption without bad taste. The pure compounds may be pre-mixed with certain dietary ingredients such as butter, olive oil, corn oil, albumin, whey or other foods which will help in absorption of the compounds by the mere process of dissolving them.

Some of the commercially available solubilizers that can be used for parenteral (injectible), oral, topical or intranasal delivery in different combinations and ratios according to need include: (a) co-solvents such as polyethylene glycol 300/400. Macrogol 300/400, Lutrol E300/E400, propylene glycol, Soluphor P and NMP; (b) PEG derivatives such as Cremophor RH40, Cremophor EL/ELP and Solutol HS-15; and (c) polyoxamers such as Lutrol F68, Lutrol F127, Lutrol Micro 68 and Lutrol Micro 127.

The compounds may be encapsulated in several weight forms (eg. 50, 100, 200, 500 mg/capsule) and taken orally. The pure compound may be mixed with excipients (eg. microcrystalline cellulose, hypermellose, magnesium stearate) to provide a mixed material that can be efficiently encapsulated by machines for mass production at a rapid rate.

The compounds may also be made into tablet form by mixing with common agents or binders used to induce adhesive properties for tablet formation.

The hydrophobic compounds may be dissolved in simple oils and applied to the skin. The compounds dissolved in DMSO (dimethylsulfoxide) are rapidly taken up through the skin without local irritation.

The compounds may also be placed in suppository capsules either in powder form or dissolved in oils or as mixed with protein based material (eg. human serum albumin) for delivery. Likewise, the compounds may also be dissolved in human serum albumin for intravenous delivery. Similarly, blood could be pulled from a patient and compounds added to that blood before being returned to the patient.

EXAMPLE 23

Mixture with oil. The compounds may be mixed with emu oil or another oil not typically used as a pharmaceutical-grade excipient but known in the art to be useful in the cosmetic and/or non-allopathic medical arts, thereby providing an OSR-oil mixture useful as an antioxidant and/or detoxicant.

EXAMPLE 24

Functional food. The compounds may be admixed with a food known in the art, thereby providing a chelator-food mixture useful as an antioxidant or detoxicant functional food.

EXAMPLE 25

Medicament useful for treating disease. A therapeutically effective medicament composition containing compounds according to the present disclosure may be administered orally to a mammalian subject, including a human, in whom it is desired to ameliorate the effect of any disease known to be associated with heavy metal toxicity and/or oxidative stress, including without limitation each disease of oxidative stress listed in Chapter 9 of Halliwell and Gutteridge 2007, op. cit. (Aspects of the relationship between oxidative stress and aging are discussed in Chapter 10 of that work).

EXAMPLE 26

Medicament and/or preparation of dosage form. To prepare a medicament and/or suitable dosage form, the compounds may be admixed and/or contacted with one or more of the excipients set forth below:

TABLE 2

| Suitable Excipients for Medicaments. |
| --- |
| Acacia |
| Acesulfame Potassium |
| Acetic Acid, Glacial |
| Acetone |
| Acetyltributyl Citrate |
| Acetyltriethyl Citrate |
| Agar |
| Albumin |
| Alcohol |
| Alginic Acid |
| Aliphatic Polyesters |
| Alitame |
| Almond Oil |
| Alpha Tocopherol |
| Aluminum Hydroxide Adjuvant |
| Aluminum Oxide |
| Aluminum Phosphate Adjuvant |
| Aluminum Stearate |
| Ammonia Solution |
| Ammonium Alginate |

TABLE 2-continued

| Suitable Excipients for Medicaments. |
| --- |
| Ascorbic Acid |
| Ascorbyl Palmitate |
| Aspartame |
| Attapulgite |
| Bentonite |
| Benzalkonium Chloride |
| Benzethonium Chloride |
| Benzoic Acid |
| Benzyl Alcohol |
| Benzyl Benzoate |
| Boric Acid |
| Bronopol |
| Butylated Hydroxyanisole |
| Butylated Hydroxytoluene |
| Butylparaben |
| Calcium Alginate |
| Calcium Carbonate |
| Calcium Phosphate, Dibasic Anhydrous |
| Calcium Phosphate, Dibasic Dihydrate |
| Calcium Phosphate, Tribasic |
| Calcium Stearate |
| Calcium Sulfate |
| Canola Oil |
| Carbomer |
| Carbon Dioxide |
| Carboxymethylcellulose Calcium |
| Carboxymethylcellulose Sodium |
| Carrageenan |
| Castor Oil |
| Castor Oil, Hydrogenated |
| Cellulose, Microcrystalline |
| Cellulose, Powdered |
| Cellulose, Silicified Microcrystalline |
| Cellulose Acetate |
| Cellulose Acetate Phthalate |
| Ceratonia |
| Cetostearyl Alcohol |
| Cetrimide |
| Cetyl Alcohol |
| Cetylpyridinium Chloride |
| Chitosan |
| Chlorhexidine |
| Chlorobutanol |
| Chlorocresol |
| Chlorodifluoroethane (HCFC) |
| Chlorofluorocarbons (CFC) |
| Chloroxylenol |
| Cholesterol |
| Citric Acid Monohydrate |
| Colloidal Silicon Dioxide |
| Coloring Agents |
| Copovidone |
| Corn Oil |
| Cottonseed Oil |
| Cresol |
| Croscarmellose Sodium |
| Crospovidone |
| Cyclodextrins |
| Cyclomethicone |
| Denatonium Benzoate |
| Dextrates |
| Dextrin |
| Dextrose |
| Dibutyl Phthalate |
| Dibutyl Sebacate |
| Diethanolamine |
| Diethyl Phthalate |
| Difluoroethane (HFC) |
| Dimethicone |
| Dimethyl Ether |
| Dimethyl Phthalate |
| Dimethyl Sulfoxide |
| Dimethylacetamide |
| Disodium Edetate |
| Docusate Sodium |
| Edetic Acid |
| Erythorbic Acid |
| Erythritol |

TABLE 2-continued

Suitable Excipients for Medicaments.

Ethyl Acetate
Ethyl Lactate
Ethyl Maltol
Ethyl Oleate
Ethyl Vanillin
Ethylcellulose
Ethylene Glycol Palmitostearate
Ethylene Vinyl Acetate
Ethylparaben
Fructose
Fumaric Acid
Gelatin
Glucose, Liquid
Glycerin
Glyceryl Behenate
Glyceryl Monooleate
Glyceryl Monostearate
Glyceryl Palmitostearate
Glycofurol
Guar Gum
Hectorite
Heptafluoropropane (HFC)
Hexetidine
Hydrocarbons (HC)
Hydrochloric Acid
Hydroxyethyl Cellulose
Hydroxyethylmethyl Cellulose
Hydroxypropyl Cellulose
Hydroxypropyl Cellulose, Low-substituted
Hydroxypropyl Starch
Hypromellose
Hypromellose Acetate Succinate
Hypromellose Phthalate
Imidurea
Inulin
Iron Oxides
Isomalt
Isopropyl Alcohol
Isopropyl Myristate
Isopropyl Palmitate
Kaolin
Lactic Acid
Lactitol
Lactose, Anhydrous
Lactose, Monohydrate
Lactose, Spray-Dried
Lanolin
Lanolin, Hydrous
Lanolin Alcohols
Lauric Acid
Lecithin
Leucine
Linoleic Acid
Macrogol 15 Hydroxystearate
Magnesium Aluminum Silicate
Magnesium Carbonate
Magnesium Oxide
Magnesium Silicate
Magnesium Stearate
Magnesium Trisilicate
Malic Acid
Maltitol
Maltitol Solution
Maltodextrin
Maltol
Maltose
Mannitol
Medium-chain Triglycerides
Meglumine
Menthol
Methylcellulose
Methylparaben
Mineral Oil
Mineral Oil, Light
Mineral Oil and Lanolin Alcohols
Monoethanolamine
Monosodium Glutamate
Monothioglycerol TABLE 2-continued Suitable Excipients for Medicaments.

Myristic Acid
Neohesperidin Dihydrochalcone
Nitrogen
Nitrous Oxide
Octyldodecanol
Oleic Acid
Oleyl Alcohol
Olive Oil
Palmitic Acid
Paraffin
Peanut Oil
Pectin
Petrolatum and Lanolin Alcohols
Petrolatum
Phenol
Phenoxyethanol
Phenylethyl Alcohol
Phenylmercuric Acetate
Phenylmercuric Borate
Phenylmercuric Nitrate
Phosphoric Acid
Polacrilin Potassium
Poloxamer
Polycarbophil
Polydextrose
Polyethylene Glycol
Polyethylene Oxide
Polymethacrylates
Poly(methyl vinyl ether/maleic anhydride)
Polyoxyethylene Alkyl Ethers
Polyoxyethylene Castor Oil Derivatives
Polyoxyethylene Sorbitan Fatty Acid Esters
Polyoxyethylene Stearates
Polyvinyl Acetate Phthalate
Polyvinyl Alcohol
Potassium Alginate
Potassium Benzoate
Potassium Bicarbonate
Potassium Chloride
Potassium Citrate
Potassium Hydroxide
Potassium Metabisulfite
Potassium Sorbate
Povidone
Propionic Acid
Propyl Gallate
Propylene Carbonate
Propylene Glycol
Propylene Glycol Alginate
Propylparaben
2-Pyrrolidone
Raffinose
Saccharin
Saccharin Sodium
Saponite
Sesame Oil
Shellac
Simethicone
Sodium Acetate
Sodium Alginate
Sodium Ascorbate
Sodium Benzoate
Sodium Bicarbonate
Sodium Borate
Sodium Chloride
Sodium Citrate Dihydrate
Sodium Cyclamate
Sodium Hyaluronate
Sodium Hydroxide
Sodium Lactate
Sodium Lauryl Sulfate
Sodium Metabisulfite
Sodium Phosphate, Dibasic
Sodium Phosphate, Monobasic
Sodium Propionate
Sodium Starch Glycolate
Sodium Stearyl Fumarate
Sodium Sulfite

TABLE 2-continued

Suitable Excipients for Medicaments.

Sorbic Acid
Sorbitan Esters (Sorbitan Fatty Acid Esters)
Sorbitol
Soybean Oil
Starch
Starch, Pregelatinized
Starch, Sterilizable Maize
Stearic Acid
Stearyl Alcohol
Sucralose
Sucrose
Sugar, Compressible
Sugar, Confectioner's
Sugar Spheres
Sulfobutylether β-Cyclodextrin
Sulfuric Acid
Sunflower Oil
Suppository Bases, Hard Fat
Talc
Tartaric Acid
Tetrafluoroethane (HFC)
Thaumatin
Thymol
Titanium Dioxide
Tragacanth
Trehalose
Triacetin
Tributyl Citrate
Triethanolamine
Triethyl Citrate
Vanillin
Vegetable Oil, Hydrogenated
Water
Wax, Anionic Emulsifying
Wax, Carnauba
Wax, Cetyl Esters
Wax, Microcrystalline
Wax, Nonionic Emulsifying
Wax, White
Wax, Yellow
Xanthan Gum
Xylitol
Zein
Zinc Acetate
Zinc Stearate

EXAMPLE 27

Dosage form. A suitable dosage form for administration of compounds according to the present disclosure may be chosen from those listed in Table 3.

TABLE 3

Dosage Forms.

| NAME | DEFINITION |
| --- | --- |
| AEROSOL | A product that is packaged under pressure and contains therapeutically active ingredients that are released upon activation of an appropriate valve system; it is intended for topical application to the skin as well as local application into the nose (nasal aerosols), mouth (lingual aerosols), or lungs (inhalation aerosols). |
| AEROSOL, POWDER | A product that is packaged under pressure and contains therapeutically active ingredients, in the form of a powder, that are released upon activation of an appropriate valve system. |
| BAR, CHEWABLE | A solid dosage form usually in the form of a rectangle that is meant to be chewed. |
| CAPSULE | A solid oral dosage form consisting of a shell and a filling. The shell is composed of a single sealed enclosure, or two halves that fit together and which are sometimes sealed with a band. Capsule shells may be made from gelatin, starch, or cellulose, or other suitable materials, may be soft or hard, and are filled with solid or liquid ingredients that can be poured or squeezed. |
| CAPSULE, COATED | A solid dosage form in which the drug is enclosed within either a hard or soft soluble container or "shell" made from a suitable form of gelatin; additionally, the capsule is covered in a designated coating. |
| CAPSULE, COATED PELLETS | A solid dosage form in which the drug is enclosed within either a hard or soft soluble container or "shell" made from a suitable form of gelatin; the drug itself is in the form of granules to which varying amounts of coating have been applied. |
| CAPSULE, COATED, EXTENDED RELEASE | A solid dosage form in which the drug is enclosed within either a hard or soft soluble container or "shell" made from a suitable form of gelatin; additionally, the capsule is covered in a designated coating, and which releases a drug (or drugs) in such a manner to allow at least a reduction in dosing frequency as compared to that drug (or drugs) presented as a conventional dosage form. |
| CAPSULE, DELAYED RELEASE | A solid dosage form in which the drug is enclosed within either a hard or soft soluble container made from a suitable form of gelatin, and which releases |

TABLE 3-continued

Dosage Forms.

| NAME | DEFINITION |
|---|---|
| | a drug (or drugs) at a time other than promptly after administration. Enteric-coated articles are delayed release dosage forms. |
| CAPSULE, DELAYED RELEASE PELLETS | A solid dosage form in which the drug is enclosed within either a hard or soft soluble container or "shell" made from a suitable form of gelatin; the drug itself is in the form of granules to which enteric coating has been applied, thus delaying release of the drug until its passage into the intestines. |
| CAPSULE, EXTENDED RELEASE | A solid dosage form in which the drug is enclosed within either a hard or soft soluble container made from a suitable form of gelatin, and which releases a drug (or drugs) in such a manner to allow a reduction in dosing frequency as compared to that drug (or drugs) presented as a conventional dosage form. |
| CAPSULE, FILM COATED, EXTENDED RELEASE | A solid dosage form in which the drug is enclosed within either a hard or soft soluble container or "shell" made from a suitable form of gelatin; additionally, the capsule is covered in a designated film coating, and which releases a drug (or drugs) in such a manner to allow at least a reduction in dosing frequency as compared to that drug (or drugs) presented as a conventional dosage form. |
| CAPSULE, GELATIN COATED | A solid dosage form in which the drug is enclosed within either a hard or soft soluble container made from a suitable form of gelatin; through a banding process, the capsule is coated with additional layers of gelatin so as to form a complete seal. |
| CAPSULE, LIQUID FILLED | A solid dosage form in which the drug is enclosed within a soluble, gelatin shell which is plasticized by the addition of a polyol, such as sorbitol or glycerin, and is therefore of a somewhat thicker consistency than that of a hard shell capsule; typically, the active ingredients are dissolved or suspended in a liquid vehicle. |
| CONCENTRATE | A liquid preparation of increased strength and reduced volume which is usually diluted prior to administration. |
| CORE, EXTENDED RELEASE | An ocular system placed in the eye from which the drug diffuses through a membrane at a constant rate over a specified period. |
| CREAM | An emulsion, semisolid[3] dosage form, usually containing >20% water and volatiles5 and/or <50% hydrocarbons, waxes, or polyols as the vehicle. This dosage form is generally for external application to the skin or mucous membranes. |
| CREAM, AUGMENTED | A cream dosage form that enhances drug delivery. Augmentation does not refer to the strength of the drug in the dosage form. NOTE: CDER has decided to refrain from expanding the use of this dosage form due to difficulties in setting specific criteria that must be met to be considered "augmented". |
| DRUG DELIVERY SYSTEM | Modern technology, distributed with or as a part of a drug product that allows for the uniform release or targeting of drugs to the body. |
| ELIXIR | A clear, pleasantly flavored, sweetened hydroalcoholic liquid containing dissolved medicinal agents; it is intended for oral use. |
| EMULSION | A dosage form consisting of a two-phase system comprised of at least two immiscible liquids[1], one of which is dispersed as droplets (internal or dispersed phase) within the other liquid (external or continuous phase), generally stabilized with one or more emulsifying agents. (Note: Emulsion is used as a dosage form term unless a more specific term is applicable, e.g. cream, lotion, ointment.) |
| ENEMA | A rectal preparation for therapeutic, diagnostic, or nutritive purposes. |
| EXTRACT | A concentrated preparation of vegetable or animal drugs obtained by removal of the active constituents of the respective drugs with a suitable menstrua, evaporation of all or nearly all of the solvent, and adjustment of the residual masses or powders to the prescribed standards. |

TABLE 3-continued

Dosage Forms.

| NAME | DEFINITION |
| --- | --- |
| FIBER, EXTENDED RELEASE | A slender and elongated solid thread-like substance that delivers drug in such a manner to allow a reduction in dosing frequency as compared to that drug (or drugs) presented as a conventional dosage form. |
| FILM, SOLUBLE | A thin layer or coating which is susceptible to being dissolved when in contact with a liquid. |
| FOR SOLUTION | A product, usually a solid, intended for solution prior to administration. |
| FOR SUSPENSION | A product, usually a solid, intended for suspension prior to administration. |
| FOR SUSPENSION, EXTENDED RELEASE | A product, usually a solid, intended for suspension prior to administration; once the suspension is administered, the drug will be released at a constant rate over a specified period. |
| GEL | A semisolid[3] dosage form that contains a gelling agent to provide stiffness to a solution or a colloidal dispersion.[4] A gel may contain suspended particles. |
| GLOBULE | Also called pellets or pilules, are made of pure sucrose, lactose, or other polysaccharides. They are formed into small globular masses of various sizes, and are medicated by placing them in a vial and adding the liquid drug attenuation in the proportion not less than one percent (v/w). After shaking, the medicated globules are dried at temperatures not to exceed 40 degrees Centigrade. |
| GRANULE | A small particle or grain. |
| GRANULE, DELAYED RELEASE | A small medicinal particle or grain to which an enteric or other coating has been applied, thus delaying release of the drug until its passage into the intestines. |
| GRANULE, EFFERVESCENT | A small particle or grain containing a medicinal agent in a dry mixture usually composed of sodium bicarbonate, citric acid, and tartaric acid which, when in contact with water, has the capability to release gas, resulting in effervescence. |
| GRANULE, FOR SOLUTION | A small medicinal particle or grain made available in its more stable dry form, to be reconstituted with solvent just before dispensing; the granules are so prepared to contain not only the medicinal agent, but the colorants, flavorants, and any other desired pharmaceutic ingredient. |
| GRANULE, FOR SUSPENSION | A small medicinal particle or grain made available in its more stable dry form, to be reconstituted with solvent just before dispensing to form a suspension; the granules are so prepared to contain not only the medicinal agent, but the colorants, flavorants, and any other desired pharmaceutic ingredient. |
| GRANULE, FOR SUSPENSION, EXTENDED RELEASE | A small medicinal particle or grain made available in its more stable dry form, to be reconstituted with solvent just before dispensing to form a suspension; the extended release system achieves slow release of the drug over an extended period of time and maintains constant drug levels in the blood or target tissue. |
| INJECTABLE, LIPOSOMAL | An injection, which either consists of or forms liposomes (a lipid bilayer vesicle usually composed of phospholipids which is used to encapsulate an active drug substance). |
| INJECTION | A sterile preparation intended for parenteral use; five distinct classes of injections exist as defined by the USP. |
| INJECTION, EMULSION | An emulsion consisting of a sterile, pyrogen-free preparation intended to be administered parenterally. |
| INJECTION, LIPID COMPLEX | [definition pending] |
| INJECTION, POWDER, FOR SOLUTION | A sterile preparation intended for reconstitution to form a solution for parenteral use. |
| INJECTION, POWDER, FOR SUSPENSION | A sterile preparation intended for reconstitution to form a suspension for parenteral use. |
| INJECTION, POWDER, FOR SUSPENSION, EXTENDED RELEASE | A dried preparation intended for reconstitution to form a suspension for parenteral use which has been formulated in a manner to allow at least a |

TABLE 3-continued

Dosage Forms.

| NAME | DEFINITION |
|---|---|
| | reduction in dosing frequency as compared to that drug presented as a conventional dosage form e.g., as a solution). |
| INJECTION, POWDER, LYOPHILIZED, FOR LIPOSOMAL SUSPENSION | A sterile freeze dried preparation intended for reconstitution for parenteral use which has been formulated in a manner that would allow liposomes (a lipid bilayer vesicle usually composed of phospholipids which is used to encapsulate an active drug substance, either within a lipid bilayer or in an aqueous space) to be formed upon reconstitution. |
| INJECTION, SUSPENSION, LIPOSOMAL | A liquid preparation, suitable for injection, which consists of an oil phase dispersed throughout an aqueous phase in such a manner that liposomes (a lipid bilayer vesicle usually composed of phospholipids which is used to encapsulate an active drug substance, either within a lipid bilayer or in an aqueous space) are formed. |
| INJECTION, SUSPENSION, SONICATED | A liquid preparation, suitable for injection, which consists of solid particles dispersed throughout a liquid phase in which the particles are not soluble. In addition, the product is sonicated while a gas is bubbled through the suspension, and this results in the formation of microspheres by the solid particles. |
| JELLY | A class of gels, which are semisolid systems that consist of suspensions made up of either small inorganic particles or large organic molecules interpenetrated by a liquid--in which the structural coherent matrix contains a high portion of liquid, usually water. |
| KIT | A packaged collection of related material. |
| LINIMENT | A solution or mixture of various substances in oil, alcoholic solutions of soap, or emulsions intended for external application. |
| LIQUID, EXTENDED RELEASE | A liquid that delivers a drug in such a manner to allow a reduction in dosing frequency as compared to that drug (or drugs) presented as a conventional dosage form. |
| LOTION | An emulsion, liquid[1] dosage form. This dosage form is generally for external application to the skin.[2] |
| LOTION, AUGMENTED | A lotion dosage form that enhances drug delivery. Augmentation does not refer to the strength of the drug in the dosage form. NOTE: CDER has decided to refrain from expanding the use of this dosage form due to difficulties in setting specific criteria that must be met to be considered "augmented". |
| LOZENGE | A solid preparation containing one or more medicaments, usually in a flavored, sweetened base which is intended to dissolve or disintegrate slowly in the mouth. A lollipop is a lozenge on a stick. |
| MOUTHWASH | An aqueous solution which is most often used for its deodorant, refreshing, or antiseptic effect. |
| OIL | An unctuous, combustible substance which is liquid, or easily liquefiable, on warming, and is soluble in ether but insoluble in water. Such substances, depending on their origin, are classified as animal, mineral, or vegetable oils. |
| OINTMENT | A semisolid[3] dosage form, usually containing <20% water and volatiles[5] and >50% hydrocarbons, waxes, or polyols as the vehicle. This dosage form is generally for external application to the skin or mucous membranes. |
| OINTMENT, AUGMENTED | An ointment dosage form that enhances drug delivery. Augmentation does not refer to the strength of the drug in the dosage form. NOTE: CDER has decided to refrain from expanding the use of this dosage form due to difficulties in setting specific criteria that must be met to be considered "augmented". |
| PASTE | A semisolid[3] dosage form, containing a large proportion (20-50%) of solids finely dispersed in a fatty vehicle. This dosage form is generally for |

TABLE 3-continued

Dosage Forms.

| NAME | DEFINITION |
|---|---|
| | external application to the skin or mucous membranes. |
| PASTILLE | An aromatic preparation, often with a pleasing flavor, usually intended to dissolve in the mouth. |
| PATCH | A drug delivery system that often contains an adhesive backing that is usually applied to an external site on the body. Its ingredients either passively diffuse from, or are actively transported from, some portion of the patch. Depending upon the patch, the ingredients are either delivered to the outer surface of the body or into the body. A patch is sometimes synonymous with the terms 'extended release film' and 'system'. |
| PATCH, EXTENDED RELEASE | A drug delivery system in the form of a patch that releases the drug in such a manner that a reduction in dosing frequency compared to that drug presented as a conventional dosage form (e.g., a solution or a prompt drug-releasing, conventional solid dosage form). |
| PATCH, EXTENDED RELEASE, ELECTRICALLY CONTROLLED | A drug delivery system in the form of a patch which is controlled by an electric current that releases the drug in such a manner that a reduction in dosing frequency compared to that drug presented as a conventional dosage form (e.g., a solution or a prompt drug-releasing, conventional solid dosage form). |
| PELLET | A small sterile solid mass consisting of a highly purified drug (with or without excipients) made by the formation of granules, or by compression and molding. |
| PELLETS, COATED, EXTENDED RELEASE | A solid dosage form in which the drug itself is in the form of granules to which varying amounts of coating have been applied, and which releases a drug (or drugs) in such a manner to allow a reduction in dosing frequency as compared to that drug (or drugs) presented as a conventional dosage form. |
| PILL | A small, round solid dosage form containing a medicinal agent intended for oral administration. |
| PLASTER | Substance intended for external application made of such materials and of such consistency as to adhere to the skin and attach to a dressing; plasters are intended to afford protection and support and/or to furnish an occlusion and macerating action and to bring medication into close contact with the skin. |
| POULTICE | A soft, moist mass of meal, herbs, seed, etc., usually applied hot in cloth that consists of gruel-like consistency. |
| POWDER | An intimate mixture of dry, finely divided drugs and/or chemicals that may be intended for internal or external use. |
| POWDER, FOR SOLUTION | An intimate mixture of dry, finely divided drugs and/or chemicals, which, upon the addition of suitable vehicles, yields a solution. |
| POWDER, FOR SUSPENSION | An intimate mixture of dry, finely divided drugs and/or chemicals, which, upon the addition of suitable vehicles, yields a suspension (a liquid preparation containing the solid particles dispersed in the liquid vehicle). |
| SALVE | A thick ointment or cerate (a fat or wax based preparation with a consistency between an ointment and a plaster). |
| SOLUTION | A clear, homogeneous liquid[1] dosage form that contains one or more chemical substances dissolved in a solvent or mixture of mutually miscible solvents. |
| SOLUTION, CONCENTRATE | A liquid preparation (i.e., a substance that flows readily in its natural state) that contains a drug dissolved in a suitable solvent or mixture of mutually miscible solvents; the drug has been strengthened by the evaporation of its nonactive parts. |
| SOLUTION, FOR SLUSH | A solution for the preparation of an iced saline slush, which is administered by irrigation and used to induce regional hypothermia (in conditions |

TABLE 3-continued

Dosage Forms.

| NAME | DEFINITION |
| --- | --- |
| | such as certain open heart and kidney surgical procedures) by its direct application. |
| SOLUTION, GEL FORMING/DROPS | A solution, which after usually being administered in a drop-wise fashion, forms a gel. |
| SOLUTION, GEL FORMING, EXTENDED RELEASE | A solution that forms a gel when it comes in contact with ocular fluid, and which allows at least a reduction in dosing frequency. |
| SOLUTION/DROPS | A solution which is usually administered in a drop-wise fashion. |
| SUPPOSITORY | A solid body of various weights and shapes, adapted for introduction into the rectal orifice of the human body; they usually melt, soften, or dissolve at body temperature. |
| SUPPOSITORY, EXTENDED RELEASE | A drug delivery system in the form of a suppository that allows for a reduction in dosing frequency. |
| SUSPENSION | A liquid1 dosage form that contains solid particles dispersed in a liquid vehicle. |
| SUSPENSION, EXTENDED RELEASE | A liquid preparation consisting of solid particles dispersed throughout a liquid phase in which the particles are not soluble; the suspension has been formulated in a manner to allow at least a reduction in dosing frequency as compared to that drug presented as a conventional dosage form (e.g., as a solution or a prompt drug-releasing, conventional solid dosage form). |
| SUSPENSION/DROPS | A suspension which is usually administered in a dropwise fashion. |
| SYRUP | An oral solution containing high concentrations of sucrose or other sugars; the term has also been used to include any other liquid dosage form prepared in a sweet and viscid vehicle, including oral suspensions. |
| TABLET | A solid dosage form containing medicinal substances with or without suitable diluents. |
| TABLET, CHEWABLE | A solid dosage form containing medicinal substances with or without suitable diluents that is intended to be chewed, producing a pleasant tasting residue in the oral cavity that is easily swallowed and does not leave a bitter or unpleasant after-taste. |
| TABLET, COATED | A solid dosage form that contains medicinal substances with or without suitable diluents and is covered with a designated coating. |
| TABLET, COATED PARTICLES | A solid dosage form containing a conglomerate of medicinal particles that have each been covered with a coating. |
| TABLET, DELAYED RELEASE | A solid dosage form which releases a drug (or drugs) at a time other than promptly after administration. Enteric-coated articles are delayed release dosage forms. |
| TABLET, DELAYED RELEASE PARTICLES | A solid dosage form containing a conglomerate of medicinal particles that have been covered with a coating which releases a drug (or drugs) at a time other than promptly after administration. Enteric-coated articles are delayed release dosage forms. |
| TABLET, DISPERSIBLE | A tablet that, prior to administration, is intended to be placed in liquid, where its contents will be distributed evenly throughout that liquid. Note: The term 'tablet, dispersible' is no longer used for approved drug products, and it has been replaced by the term 'tablet, for suspension'. |
| TABLET, EFFERVESCENT | A solid dosage form containing mixtures of acids (e.g., citric acid, tartaric acid) and sodium bicarbonate, which release carbon dioxide when dissolved in water; it is intended to be dissolved or dispersed in water before administration. |
| TABLET, EXTENDED RELEASE | A solid dosage form containing a drug which allows at least a reduction in dosing frequency as compared to that drug presented in conventional dosage form. |
| TABLET, FILM COATED | A solid dosage form that contains medicinal substances with or without suitable diluents and is coated with a thin layer of a water-insoluble or water-soluble polymer. |

TABLE 3-continued

Dosage Forms.

| NAME | DEFINITION |
|---|---|
| TABLET, FILM COATED, EXTENDED RELEASE | A solid dosage form that contains medicinal substances with or without suitable diluents and is coated with a thin layer of a water-insoluble or water-soluble polymer; the tablet is formulated in such manner as to make the contained medicament available over an extended period of time following ingestion. |
| TABLET, FOR SOLUTION | A tablet that forms a solution when placed in a liquid. |
| TABLET, FOR SUSPENSION | A tablet that forms a suspension when placed in a liquid (formerly referred to as a 'dispersible tablet'). |
| TABLET, MULTILAYER | A solid dosage form containing medicinal substances that have been compressed to form a multiple-layered tablet or a tablet-within-a-tablet, the inner tablet being the core and the outer portion being the shell. |
| TABLET, MULTILAYER, EXTENDED RELEASE | A solid dosage form containing medicinal substances that have been compressed to form a multiple-layered tablet or a tablet-within-a-tablet, the inner tablet being the core and the outer portion being the shell, which, additionally, is covered in a designated coating; the tablet is formulated in such manner as to allow at least a reduction in dosing frequency as compared to that drug presented as a conventional dosage form. |
| TABLET, ORALLY DISINTEGRATING | A solid dosage form containing medicinal substances which disintegrates rapidly, usually within a matter of seconds, when placed upon the tongue. |
| TABLET, ORALLY DISINTEGRATING, DELAYED RELEASE | A solid dosage form containing medicinal substances which disintegrates rapidly, usually within a matter of seconds, when placed upon the tongue, but which releases a drug (or drugs) at a time other than promptly after administration. |
| TABLET, SOLUBLE | A solid dosage form that contains medicinal substances with or without suitable diluents and possesses the ability to dissolve in fluids. |
| TABLET, SUGAR COATED | A solid dosage form that contains medicinal substances with or without suitable diluents and is coated with a colored or an uncolored water-soluble sugar. |

Footnotes:
[1] A liquid is pourable; it flows and conforms to its container at room temperature. It displays Newtonian or pseudoplastic flow behavior.
[2] Previously the definition of a lotion was "The term lotion has been used to categorize many topical suspensions, solutions, and emulsions intended for application to the skin." The current definition of a lotion is restricted to an emulsion.
[3] A semisolid is not pourable; it does not flow or conform to its container at room temperature. It does not flow at low shear stress and generally exhibits plastic flow behavior.
[4] A colloidal dispersion is a system in which particles of colloidal dimension (i.e., typically between 1 nm and 1 μm) are distributed uniformly throughout a liquid.
[5] Percent water and volatiles are measured by a loss on drying test in which the sample is heated at 105° C. until constant weight is achieved.

EXAMPLE 28

Route of administration. A suitable route of administration for a dosage form containing compounds according to the present disclosure may be chosen from those listed in Table 4.

TABLE 4

Routes of Administration.
Routes of administration

| NAME | DEFINITION |
|---|---|
| BUCCAL | Administration directed toward the cheek, generally from within the mouth. |
| CONJUNCTIVAL | Administration to the conjunctiva, the delicate membrane that lines the eyelids and covers the exposed surface of the eyeball. |
| CUTANEOUS | Administration to the skin. |
| ENDOSINUSIAL | Administration within the nasal sinuses of the head. |

TABLE 4-continued

Routes of Administration.
Routes of administration

| NAME | DEFINITION |
| --- | --- |
| ENTERAL | Administration directly into the intestines. |
| EPIDURAL | Administration upon or over the dura mater. |
| EXTRACORPOREAL | Administration outside of the body. |
| HEMODIALYSIS | Administration through hemodialysate fluid. |
| INFILTRATION | Administration that results in substances passing into tissue spaces or into cells. |
| INTERSTITIAL | Administration to or in the interstices of a tissue. |
| INTRA-ABDOMINAL | Administration within the abdomen. |
| INTRA-ARTERIAL | Administration within an artery or arteries. |
| INTRA-ARTICULAR | Administration within a joint. |
| INTRACARTILAGINOUS | Administration within a cartilage; endochondral. |
| INTRACAUDAL | Administration within the cauda equina. |
| INTRACORONARY | Administration within the coronary arteries. |
| INTRADERMAL | Administration within the dermis. |
| INTRADUCTAL | Administration within the duct of a gland. |
| INTRADUODENAL | Administration within the duodenum. |
| INTRADURAL | Administration within or beneath the dura. |
| INTRAEPIDERMAL | Administration within the epidermis. |
| INTRAESOPHAGEAL | Administration within the esophagus. |
| INTRAGASTRIC | Administration within the stomach. |
| INTRAGINGIVAL | Administration within the gingivae. |
| INTRALYMPHATIC | Administration within the lymph. |
| INTRAMEDULLARY | Administration within the marrow cavity of a bone. |
| INTRAMENINGEAL | Administration within the meninges (the three membranes that envelope the brain and spinal cord). |
| INTRAMUSCULAR | Administration within a muscle. |
| INTRAOCULAR | Administration within the eye. |
| INTRAOVARIAN | Administration within the ovary. |
| INTRAPERICARDIAL | Administration within the pericardium. |
| INTRAPERITONEAL | Administration within the peritoneal cavity. |
| INTRAPLEURAL | Administration within the pleura. |
| INTRAPULMONARY | Administration within the lungs or its bronchi. |
| INTRASINAL | Administration within the nasal or periorbital sinuses. |
| INTRASPINAL | Administration within the vertebral column. |
| INTRASYNOVIAL | Administration within the synovial cavity of a joint. |
| INTRATENDINOUS | Administration within a tendon. |
| INTRATHECAL | Administration within the cerebrospinal fluid at any level of the cerebrospinal axis, including injection into the cerebral ventricles. |
| INTRATHORACIC | Administration within the thorax (internal to the ribs); synonymous with the term endothoracic. |
| INTRATUMOR | Administration within a tumor. |
| INTRAUTERINE | Administration within the uterus. |
| INTRAVASCULAR | Administration within a vessel or vessels. |
| INTRAVENOUS | Administration within or into a vein or veins. |
| INTRAVENOUS BOLUS | Administration within or into a vein or veins all at once. |
| INTRAVENOUS DRIP | Administration within or into a vein or veins over a sustained period of time. |
| INTRAVENTRICULAR | Administration within a ventricle. |
| INTRAVESICAL | Administration within the bladder. |
| INTRAVITREAL | Administration within the vitreous body of the eye. |
| NASAL | Administration to the nose; administered by way of the nose. |
| OPHTHALMIC | Administration to the external eye. |
| ORAL | Administration to or by way of the mouth. |
| OROPHARYNGEAL | Administration directly to the mouth and pharynx. |
| OTHER | Administration is different from others on this list. |
| PARENTERAL | Administration by injection, infusion, or implantation. |
| PERCUTANEOUS | Administration through the skin. |

TABLE 4-continued

Routes of Administration.
Routes of administration

| NAME | DEFINITION |
| --- | --- |
| PERIARTICULAR | Administration around a joint. |
| PERIDURAL | Administration to the outside of the duramater of the spinal cord . . . |
| PERINEURAL | Administration surrounding a nerve or nerves. |
| PERIODONTAL | Administration around a tooth. |
| RECTAL | Administration to the rectum. |
| RESPIRATORY (INHALATION) | Administration within the respiratory tract by inhaling orally or nasally for local or systemic effect. |
| SOFT TISSUE | Administration into any soft tissue. |
| SUBCONJUNCTIVAL | Administration beneath the conjunctiva. |
| SUBCUTANEOUS | Administration beneath the skin; hypodermic. Synonymous with the term SUBDERMAL. |
| SUBLINGUAL | Administration beneath the tongue. |
| SUBMUCOSAL | Administration beneath the mucous membrane. |
| TOPICAL | Administration to a particular spot on the outer surface of the body. The E2B term TRANSMAMMARY is a subset of the term TOPICAL. |
| TRANSDERMAL | Administration through the dermal layer of the skin to the systemic circulation by diffusion. |
| TRANSMUCOSAL | Administration across the mucosa. |

It is noted that terms like "preferably," "commonly," and "typically" are not utilized herein to limit the scope of the disclosure or to imply that certain features are critical, essential, or even important to the structure or function of the disclosure. Rather, these terms are merely intended to highlight alternative or additional features that may or may not be utilized in a particular embodiment of the present disclosure.

For the purposes of describing and defining the present disclosure it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the disclosure in detail and by reference to specific embodiments thereof, it will be apparent that modifications and variations are possible without departing from the scope of the disclosure. More specifically, although some aspects of the present disclosure are identified as advantageous, it is contemplated that the present disclosure is not necessarily limited to these aspects of the disclosure.

What is claimed is:

1. A method for ameliorating heavy metal toxicity in a mammal, comprising administering to the mammal a pharmaceutically effective amount of a compound having a chemical formula:

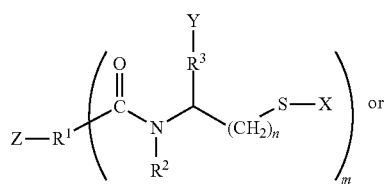

where $R^1$ is selected from the group consisting of benzene, pyridine, pyridin-4-one, naphthalene, anthracene, and phenanthrene groups, $R^2$ is independently selected from the group consisting of hydrogen, alkyls, aryls, a carboxyl group, and carboxylate esters, $R^3$ is independently selected from the group consisting of benzene alkyls, aryls, a carboxyl group, and carboxylate esters, X is independently selected from the group consisting of benzene hydrogen, lithium, sodium, potassium, rubidium, cesium, francium, alkyls, aryls, a carboxyl group, carboxylate esters, cysteine, homocysteine, glutathione, lipoic acid, dihydrolipoic acid, thiophosphate, N-acetyl cysteine, mercaptoacetic acid, mercaptopropionic acid, γ-glutamyl cysteine, phytochelatins, and thiolsalicylate, n independently equals 1-10, m=2, 4, 5, or 6, Y is independently selected from the group consisting of hydrogen, polymers, silicas and silica supported substrates, and Z is selected from the group consisting of hydrogen, alkyls, aryls, a carboxyl group, carboxylate esters, a hydroxyl group, $NH_2$, $HSO_3$, halogens, a carbonyl group, polymers, silicas and silica supported substrates.

2. The method of claim 1, wherein m=2.

3. The method of claim 2, wherein at least one $R^3$ is a carboxyl group.

4. The method of claim 3, wherein at least one X is glutathione.

5. The method of claim 3, wherein at least one $R^3$ is a carboxylic acid, a methyl-ester or an ethyl-ester.

6. The method of claim 1, wherein both $R^2$ are hydrogen, both $R^3$ are a carboxyl group, both X are glutathione and both n equal 1.

7. The method of claim 1, wherein $R^1$ is benzene.

8. The method of claim 1, including selecting a route of administration from at least one of the group consisting of oral, transmucosal, transdermal, nasal, suppository, intravenous, and combinations thereof.

9. The method of claim 8, including administering between about 0.5 and 100 milligrams of the compound per kilogram of the mammal's total body weight.

10. The method of claim 9, including administering between about 0.5 and 60 milligrams of the compound per kilogram of the mammal's total body weight.

11. A method for relieving oxidative stress in a mammal, comprising administering to the mammal a pharmaceutically effective amount of a compound having a chemical formula:

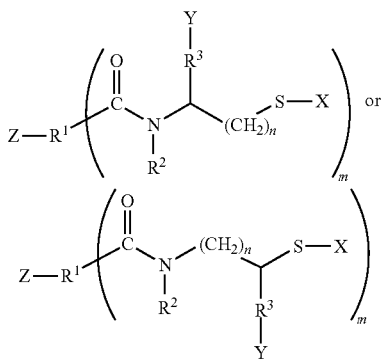

where $R^1$ is selected from the group consisting of benzene, pyridine, pyridin-4-one, naphthalene, anthracene, and phenanthrene groups, $R^2$ is independently selected from the group consisting of hydrogen, alkyls, aryls, a carboxyl group, and carboxylate esters, $R^3$ is independently selected from the group consisting of benzene alkyls, aryls, a carboxyl group, and carboxylate esters, X is independently selected from the group consisting of benzene hydrogen, lithium, sodium, potassium, rubidium, cesium, francium, alkyls, aryls, a carboxyl group, carboxylate esters, cysteine, homocysteine, glutathione, lipoic acid, dihydrolipoic acid, thiophosphate, N-acetyl cysteine, mercaptoacetic acid, mercaptopropionic acid, γ-glutamyl cysteine, phytochelatins, and thiolsalicylate, n independently equals 1-10, m=2, 4, 5, or 6, Y is independently selected from the group consisting of hydrogen, polymers, silicas and silica supported substrates, and Z is selected from the group consisting of hydrogen, alkyls, aryls, a carboxyl group, carboxylate esters, a hydroxyl group, $NH_2$, $HSO_3$, halogens, a carbonyl group, polymers, silicas and silica supported substrates.

12. The method of claim 11, wherein m=2.

13. The method of claim 12, wherein at least one $R^3$ is a carboxyl group.

14. The method of claim 13, wherein at least one X is glutathione.

15. The method of claim 13, wherein at least one $R^3$ is a carboxylic acid, a methyl-ester or an ethyl-ester.

16. The method of claim 11, wherein $R^1$ is benzene.

17. The method of claim 11, including selecting a route of administration from at least one of the group consisting of oral, transmucosal, transdermal, nasal, suppository, intravenous, and combinations thereof.

18. The method of claim 17, including administering between about 0.5 and 100 milligrams of the compound per kilogram of the mammal's total body weight.

19. The method of claim 18, including administering between about 0.5 and 60 milligrams of the compound per kilogram of the mammal's total body weight.

20. The method of claim 14, wherein at least one $R^3$ is a carboxyl group.

21. A method for ameliorating heavy metal toxicity in a mammal, comprising administering to the mammal a pharmaceutically effective amount of a compound having a chemical formula:

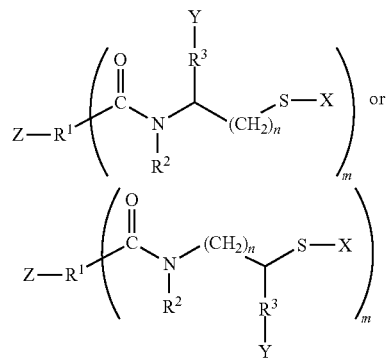

where $R^1$ is selected from the group consisting of benzene, pyridine, pyridin-4-one, naphthalene, anthracene, and phenanthrene groups, $R^2$ is independently selected from the group consisting of hydrogen, alkyls, aryls, a carboxyl group, and carboxylate esters, $R^3$ is independently selected from the group consisting of benzene alkyls, aryls, a carboxyl group, and carboxylate esters, X is independently selected from the group consisting of benzene hydrogen, lithium, sodium, potassium, rubidium, cesium, francium, alkyls, aryls, a carboxyl group, carboxylate esters, cysteine, homocysteine, glutathione, lipoic acid, dihydrolipoic acid, thiophosphate, N-acetyl cysteine, mercaptoacetic acid, mercaptopropionic acid, γ-glutamyl cysteine, phytochelatins, and thiolsalicylate, n independently equals 1-10, m=2, 4, 5, or 6, Y is independently selected from the group consisting of hydrogen, polymers, silicas and silica supported substrates, and Z is selected from the group consisting of hydrogen, alkyls, aryls, a carboxyl group, carboxylate esters, a hydroxyl group, $NH_2$, $HSO_3$, halogens, a carbonyl group, polymers, silicas and silica supported substrates;

wherein at least one of said $R^3$ and said X group is selected whereby a property of hydrophobicity or hydrophilicity of said compound is selectively altered, said property of hydrophobicity or hydrophilicity in turn determining whether said compound having a heavy metal bound thereto is cleared from the mammal body via a fecal route or a kidney route.

22. The method of claim 21, wherein m=2.

23. The method of claim 22, wherein at least one $R^3$ is a methyl-ester or an ethyl-ester.

24. The method of claim 21, wherein $R^1$ is benzene.

25. The method of claim 21, including selecting a route of administration from at least one of the group consisting of oral, transmucosal, transdermal, nasal, suppository, intravenous, and combinations thereof.

* * * * *